US009676702B2

(12) United States Patent
Lutz et al.

(10) Patent No.: US 9,676,702 B2
(45) Date of Patent: Jun. 13, 2017

(54) METHODS FOR SYNTHESIZING AMATOXIN BUILDING BLOCK AND AMATOXINS

(71) Applicant: Heidelberg Pharma GmbH, Ladenburg (DE)

(72) Inventors: Christian Lutz, Weinheim (DE); Christoph Mueller, Birkenau (DE); Werner Simon, Hueffelsheim (DE)

(73) Assignee: Heidelberg Pharma GmbH (DE)

( * ) Notice: Subject to any disclaimer, the term of this patent is extended or adjusted under 35 U.S.C. 154(b) by 0 days.

(21) Appl. No.: 14/414,143

(22) PCT Filed: Jul. 12, 2013

(86) PCT No.: PCT/EP2013/002084

§ 371 (c)(1),
(2) Date: Jan. 12, 2015

(87) PCT Pub. No.: WO2014/009025

PCT Pub. Date: Jan. 16, 2014

(65) Prior Publication Data

US 2015/0210628 A1 Jul. 30, 2015

(30) Foreign Application Priority Data

Jul. 13, 2012 (EP) .................................... 12005173

(51) Int. Cl.

| | |
|---|---|
| ***A61K 31/33*** | (2006.01) |
| ***C07D 487/04*** | (2006.01) |
| ***C07C 227/16*** | (2006.01) |
| ***C07C 229/22*** | (2006.01) |
| ***C07K 1/06*** | (2006.01) |
| ***C07D 207/16*** | (2006.01) |
| ***C07K 1/10*** | (2006.01) |

(52) U.S. Cl.

CPC .......... *C07C 227/16* (2013.01); *C07C 229/22* (2013.01); *C07D 207/16* (2013.01); *C07K 1/065* (2013.01); *C07K 1/10* (2013.01)

(58) Field of Classification Search

None

See application file for complete search history.

(56) References Cited

U.S. PATENT DOCUMENTS

| | | |
|---|---|---|
| 4,128,542 A | 12/1978 | Atherton et al. |
| 6,743,807 B2 | 6/2004 | Duan et al. |
| 2012/0213805 A1 | 8/2012 | Faulstich et al. |

FOREIGN PATENT DOCUMENTS

| | | |
|---|---|---|
| CA | 2060856 | 8/1992 |
| CN | 102387815 A | 3/2012 |
| JP | S53-9761 | 1/1978 |
| JP | H5-105656 | 4/1993 |
| JP | H9-59228 | 3/1997 |
| JP | H11137291 A | 5/1999 |
| JP | 2002-516337 | 6/2002 |
| JP | 2003-528072 | 9/2003 |
| JP | 2004-501085 | 1/2004 |
| WO | 99/61466 | 12/1999 |
| WO | 01/79242 | 10/2001 |
| WO | 2010115629 A2 | 10/2010 |

OTHER PUBLICATIONS

Zanotti et al. (Synthesis of analogues of amaninamide, an amatoxin from the white Arnanita virosa mushroom, Int. J. Peptide Protein Res., Jan. 1, 1987).*

First Office Action from Chinese Patent Application No. 201380037459.2 dated Sep. 30, 2015.

Guo, et al. Culture Conditions and Analysis of Amanitins on Amanita Spissa, Acta Microbiologica Sinica, 46(3), Jun. 4, 2006, pp. 373-378.

Yoshida et al. A Large-Scale Preparation of (3S,4S)-3-(tert-Butoxycarbonyl) amino-4-methylpyrrolidine and its Analogs from L-Aspartic Acid, Chem. Pharm. Bull 44(5), May 1996 pp. 1128-1131.

Giancarlo Zanotti et al: "Synthesis of Analogues of Amaninamide, an Amatoxin From the White Arnanita Virosa Mushroom" J. Peptide Protein Res., pp. 450-459 (dated Jan. 1, 1987).

TH. Wieland et al: "Die Absoluten Konfigurationen der in den Phytotoxinen Enthaltenen gamma-Hydroxyaminosauren und der gamma-Hydroxynorvaline" Liebigs Ann. Chem. vol. 717, pp. 205-214 (dated 1968).

International Search Report and Written Opinion for PCT/EP2013/002084 (dated Sep. 13, 2013).

Office Action from Japanese Application No. 2015-520852 dated Feb. 7, 2017.

Zanotti et al., "Structure-toxicity relationships in the amatoxin series," Int. J. Peptid Protein Res., vol. 40, 1992, pp. 551-558.

* cited by examiner

*Primary Examiner* — Jeanette Lieb
(74) *Attorney, Agent, or Firm* — Calfee, Halter & Griswold LLP

(57) ABSTRACT

The invention relates to novel methods for synthesizing a synthon for γ,δ-dihydroxyisoleucine 1 (CAS No. 55399-94-5] as building block for the synthesis of amatoxins, and for novel methods for synthesizing amatoxins using such building block.

1

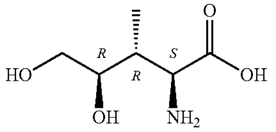

[55399-94-5]

19 Claims, 3 Drawing Sheets

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |

Fmoc: Fluorenylmethoxycarbonyl protection group

METHODS FOR SYNTHESIZING AMATOXIN BUILDING BLOCK AND AMATOXINS

CROSS-REFERENCE TO RELATED APPLICATIONS

This application is the U.S. national phase entry of PCT/EP2013/002084, with an international filing date of 12 Jul. 2013, which claims the benefit of European patent application no. 12005173.5, with a filing date of 13 Jul. 2012, the entire disclosures of which are fully incorporated herein by reference.

FIELD OF THE INVENTION

The invention relates to novel methods for synthesizing a synthon for γ,δ-dihydroxyisoleucine 1 (CAS No. 55399-94-5] as building block for the synthesis of amatoxins, and for novel methods for synthesizing amatoxins using such building block.

1

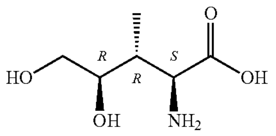

[55399-94-5]

BACKGROUND OF THE INVENTION

Amatoxins are cyclic peptides composed of 8 amino acids, that are found in *Amanita phalloides* mushrooms (see FIG. 1). Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA-polymerase II is very tight ($K_D$=3 nM). Dissociation of amanitin from the enzyme is a very slow process, thus making recovery of an affected cell unlikely. When the inhibition of transcription lasts too long, the cell will undergo programmed cell death (apoptosis).

The use of amatoxins as cytotoxic moieties for tumour therapy had already been explored in 1981 by coupling an anti-Thy 1.2 antibody to α-amanitin using a linker attached to the indole ring of Trp (amino acid 4; see FIG. 1) via diazotation (Davis & Preston, Science 1981, 213, 1385-1388). Davis & Preston identified the site of attachment as position 7'. Morris & Venton demonstrated as well that substitution at position 7' results in a derivative, which maintains cytotoxic activity (Morris & Venton, Int. J. Peptide Protein Res. 1983, 21 419-430).

Patent application EP 1 859 811 A1 (published Nov. 28, 2007) described conjugates, in which the γ C-atom of amatoxin amino acid 1 of β-amanitin was directly coupled, i.e. without a linker structure, to albumin or to monoclonal antibody HEA125, OKT3, or PA-1. Furthermore, the inhibitory effect of these conjugates on the proliferation of breast cancer cells (MCF-7), Burkitt's lymphoma cells (Raji), and T-lymphoma cells (Jurkat) was shown. The use of linkers was suggested, including linkers comprising elements such as amide, ester, ether, thioether, disulfide, urea, thiourea, hydrocarbon moieties and the like, but no such constructs were actually shown, and no more details, such as attachment sites on the amatoxins, were provided.

Patent applications WO 2010/115629 and WO 2010/115630 (both published Oct. 14, 2010) describe conjugates, where antibodies, such as anti-EpCAM antibodies such as humanized antibody huHEA125, are coupled to amatoxins via (i) the γ C-atom of amatoxin amino acid 1, (ii) the 6' C-atom of amatoxin amino acid 4, or (iii) via the δ C-atom of amatoxin amino acid 3, in each case either directly or via a linker between the antibody and the amatoxins. The suggested linkers comprise elements such as amide, ester, ether, thioether, disulfide, urea, thiourea, hydrocarbon moieties and the like. Furthermore, the inhibitory effects of these conjugates on the proliferation of breast cancer cells (cell line MCF-7), pancreatic carcinoma (cell line Capan-1), colon cancer (cell line Colo205), and cholangiocarcinoma (cell line OZ) were shown.

Amatoxins can be isolated from collected *Amanita phalloides* mushrooms fruit bodies, or from pure cultures (Zhang P, Chen Z, Hu J, Wei B, Zhang Z, and Hu W, Production and characterization of Amanitin toxins from a pure culture of *Amanita exitialis*, FEMS Microbiol Lett. 2005 Nov. 15;252 (2):223-8. Epub 2005 Sep. 15). However, the amounts of amatoxins that can be obtained are rather low (in the range of about 0.3-3 mg/g dry matter from natural fruit bodies, and about 10% thereof from pure culture) and the flexibility for further modifying the naturally occurring amatoxin variants is limited.

Alternatively, amatoxins can be obtained from fermentation using a basidiomycete (Muraoka S, and Shinozawa T., Effective production of amanitins by two-step cultivation of the basidiomycete, Galerina fasciculata GF-060, J Biosci Bioeng. 2000; 89(1):73-6; the reported yield was about 5 mg/l culture) or *A. fissa* (Guo X W, Wang G L, and Gong J H, Culture conditions and analysis of amanitins on *Amanita spissa*, Wei Sheng Wu Xue Bao. 2006 June; 46(3):373-8; the reported yield was about 30 μg/l culture). Again, yields are low, and flexibility for further modifying the naturally occurring amatoxin variants is limited as well.

Finally, amatoxins have been prepared by partial or total synthesis (e.g. Zanotti G, Möhringer C, and Wieland T., Synthesis of analogues of amaninamide, an amatoxin from the white *Amanita virosa* mushroom, Int J Pept Protein Res. 1987 October; 30(4):450-9; Zanotti G, Wieland T, Benedetti E, Di Blasio B, Pavone V, and Pedone C., Structure-toxicity relationships in the amatoxin series. Synthesis of S-deoxy [gamma(R)-hydroxy-Ile3]-amaninamide, its crystal and molecular structure and inhibitory efficiency, Int J Pept Protein Res. 1989 September; 34(3):222-8; Zanotti G, Petersen G, and Wieland T., Structure-toxicity relationships in the amatoxin series. Structural variations of side chain 3 and inhibition of RNA polymerase II, Int J Pept Protein Res. 1992 December; 40(6):551-8).

While the use of fully-synthetic routes to amatoxins may offer the supply of larger quantities of amatoxins required for therapeutic uses, and may offer the construction of a variety of novel amatoxin variants by using appropriate starting materials as building blocks, no fully-synthetic approach to the most relevant amatoxins, α-amanitin and β-amanitin, as well as amanin and amaninamide, has been reported so far. This may, at least in part, be attributable to the fact that an essential building block, γ, δ-dihydroxyisoleucine 1 or a synthon therefor, was not yet available so far as pure diastereomer.

SUMMARY OF THE INVENTION

The present invention is based on the unexpected observation that γ,δ-dihydroxyisoleucine 1, or a synthon therefore, can be obtained in a multi-step process, wherein the regioselective methylation of an appropriately protected aspartic acid derivative is the key step.

Thus, in one aspect the present invention relates to a method for the synthesis of γ,δ-dihydroxyisoleucine 1, or of a synthon for compound 1, comprising the step of methylating compound 3, particularly with methyl iodide in the presence of lithium bis(trimethylsilyl)amide (LHMDS).

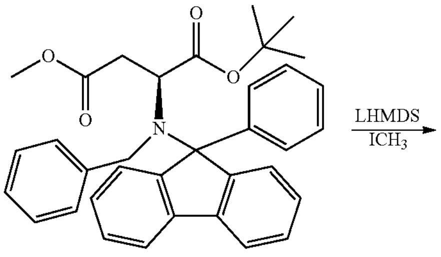

3

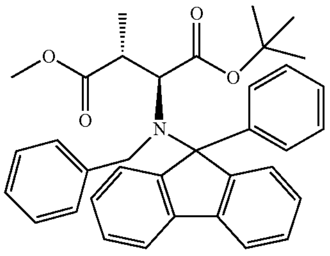

2

In an alternative aspect, the present invention relates to a method for the synthesis of γ,δ-dihydroxyisoleucine 1, or of a synthon for compound 1, comprising the step of methylating compound 3* (having a second benzyl protection group at the nitrogen atom instead of the phenyl fluorenyl group in compound 3), particularly with methyl iodide in the presence of lithium bis(trimethylsilyl)amide (LHMDS).

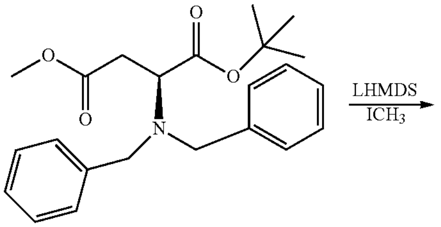

3*

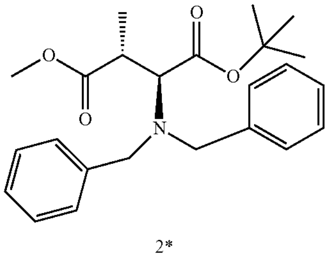

2*

In a second aspect, the present invention relates to compound 6.

6

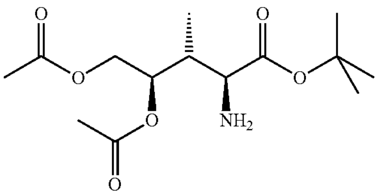

In a third aspect, the present invention relates to a kit comprising compound 6, and at least one additional reagent for the synthesis of amatoxins or precursors thereof.

In yet another aspect, the present invention relates to a method for synthesizing an amatoxin, or precursor molecule therefor, comprising the step of coupling compound 6 to hydroxyproline, particularly by reacting compound 6 with a hydroxyproline-preloaded resin (PS) L.

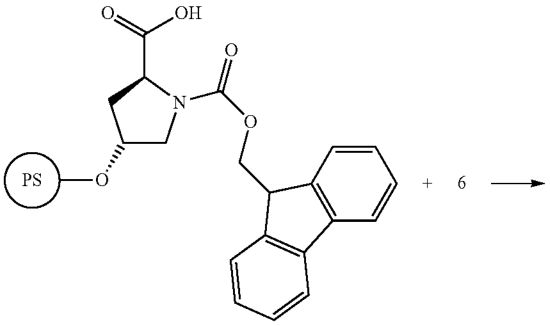

L

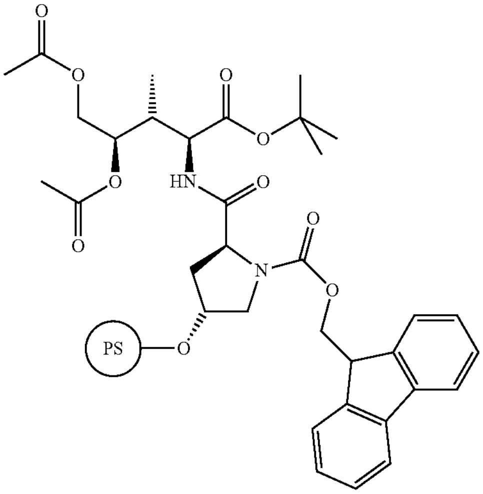

G

DETAILED DESCRIPTION OF THE INVENTION

Figure 1:
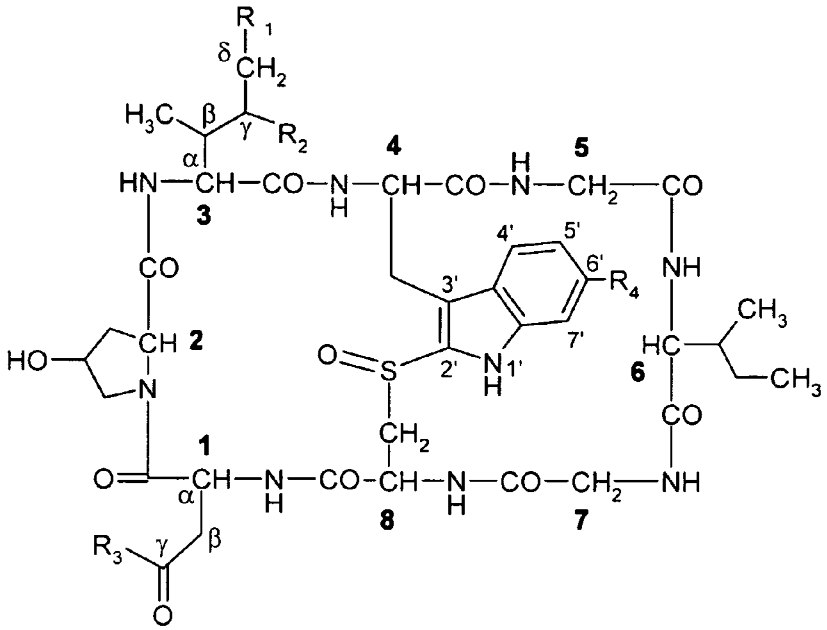
FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters α to γ, Greek letters α to δ, and numbers from 1' to 7', respectively).
Figure 2:
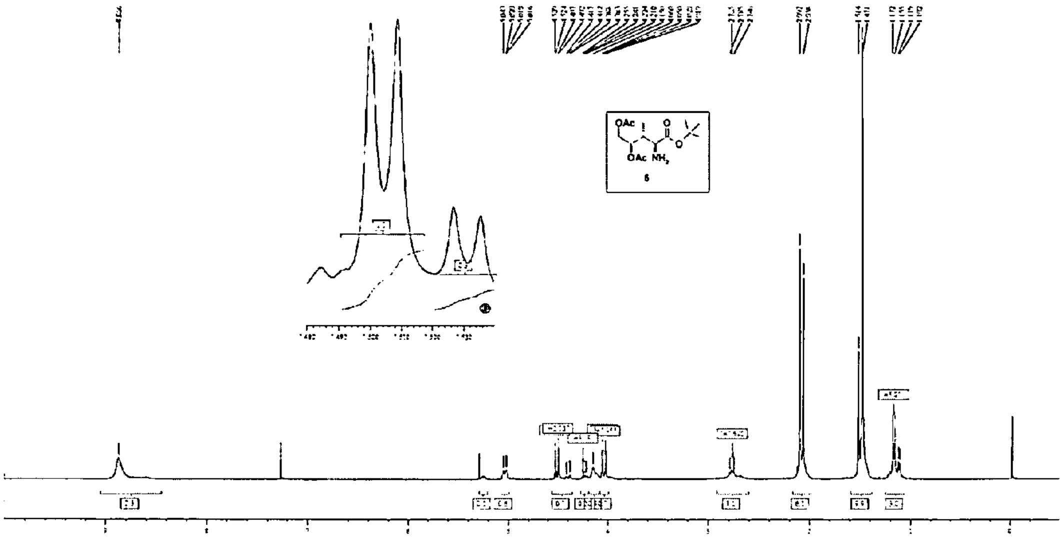
FIG. 2 shows $^1$H- and $^{13}$C-NMR spectra, displaying a diastereomeric ratio of 70:30 of compound 6.
Figure 2:
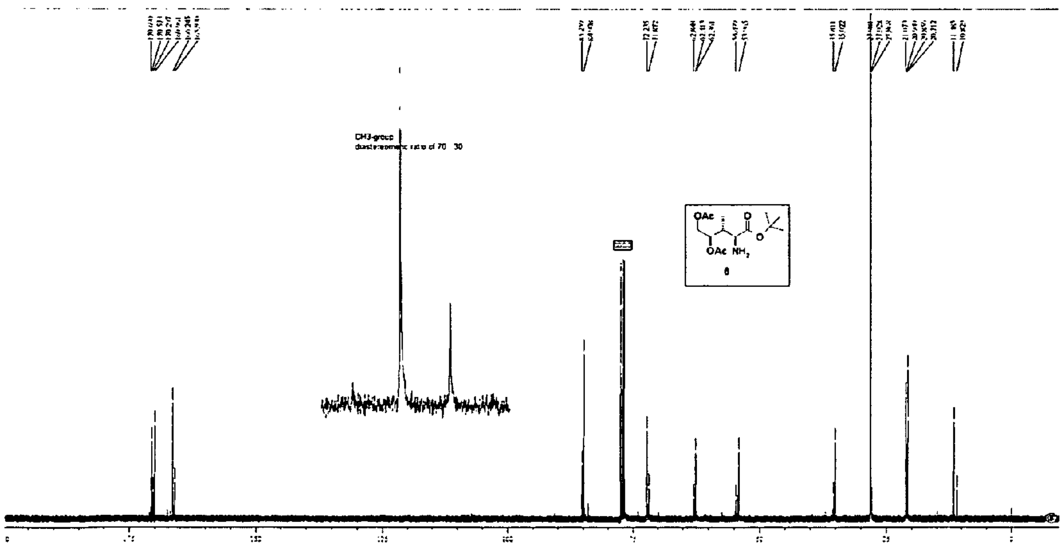
Figure 3:
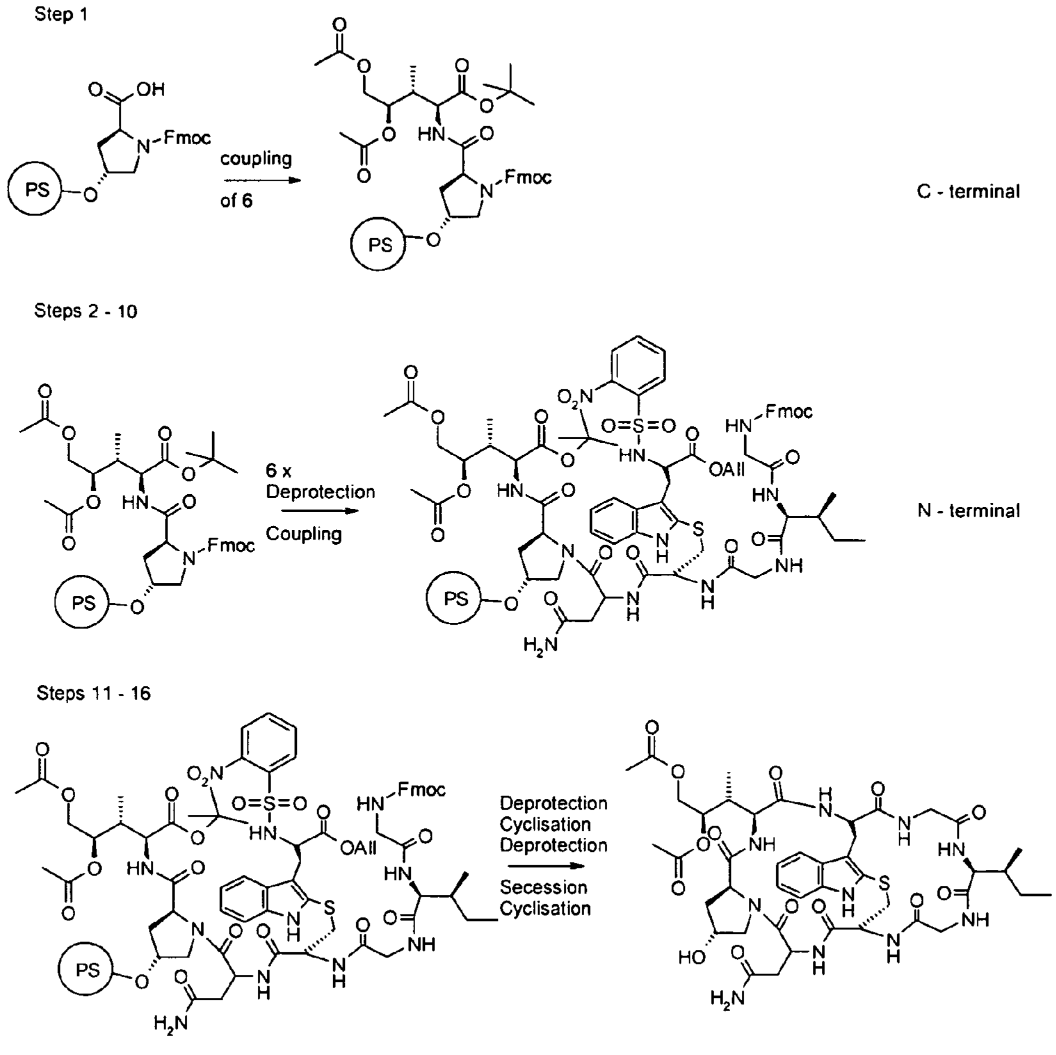
FIG. 3 shows a general synthetic scheme of the synthesis of amatoxins.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer, composition or step or group of integers or steps, while any additional integer, composition or step or group of integers, compositions or steps may optionally be present as well, including embodiments, where no additional integer, composition or step or group of integers, compositions or steps are present. In such latter embodiments, the term "comprising" is used coterminous with "consisting of".

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law. Nothing herein is to be construed as an admission that the invention is not entitled to antedate such disclosure by virtue of prior invention.

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Thus, in one aspect the present invention relates to a method for the synthesis of γ,δ-dihydroxyisoleucine 1, or of a synthon for compound 1, comprising the step of methylating compound 3, particularly with methyl iodide in the presence of lithium bis(trimethylsilyl)amide (LHMDS).

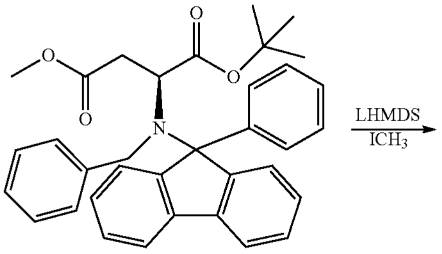

3

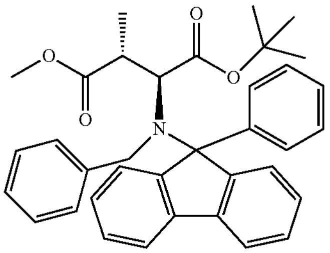

2

In an alternative aspect, the present invention relates to a method for the synthesis of γ,δ-dihydroxyisoleucine 1, or of a synthon for compound 1, comprising the step of methylating compound 3* (having a second benzyl protection group at the nitrogen atom instead of the phenyl fluorenyl group in compound 3), particularly with methyl iodide in the presence of lithium bis(trimethylsilyl)amide (LHMDS).

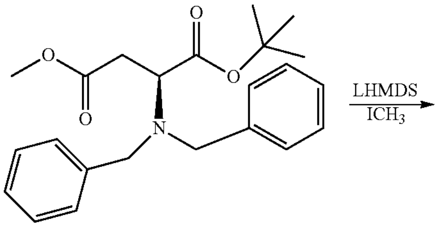

3*

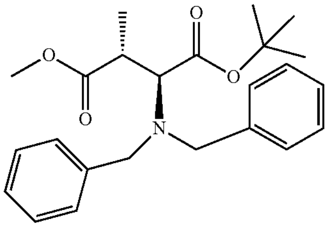

2*

In the context of the present invention, the term "synthon" refers to a compound that is, or can be used as, a synthetic equivalent for a particular compound of interest in a chemical reaction. This definition includes compounds, where a moiety of the compound of interest that would be labile or reactive under the conditions to be used in said chemical reaction is protected or masked by an appropriate protection group that can be cleaved off after said chemical reaction.

In a particular embodiment, the reaction is performed at a temperature between about −10° C. and about −80° C. in an ether for between about 12 and about 20 hours, particularly for about 16 hours. In a particular embodiment, the reaction is performed at −20° C. and in tetrahydrofuran as solvent. In particular embodiments, a diastereomeric purity of greater than 30:1, particularly greater than 40:1, particularly about 50:1 is obtained.

In the context of the present invention, the term “about” or “approximately” means between 90% and 110% of a given value or range.

In a particular embodiment, the method further comprises one or more of the following steps for synthesizing compound 3:

(a) reaction of L-aspartic acid, monomethyl ester A with 2-methyl propene to create compound B;

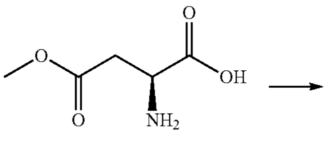

A

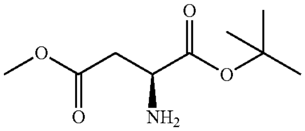

B (b) reaction of B with benzaldehyde to create compound C;

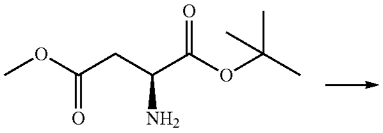

B

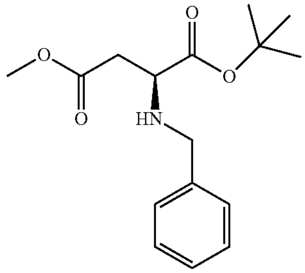

C (c) reaction of C with phenyl fluorene bromide to create compound 3.

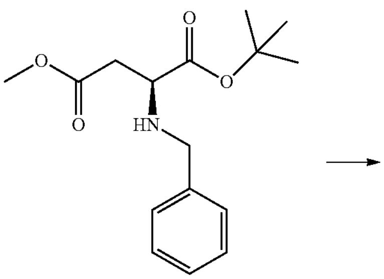

C

-continued

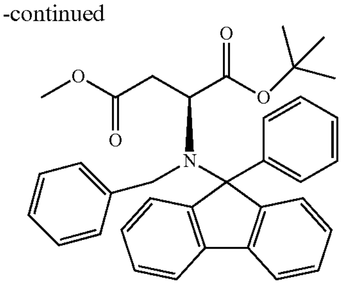

3

In an embodiment of the alternative aspect, the method further comprises one or more of the following steps for synthesizing compound 3*:

(a) reaction of L-aspartic acid, monomethyl ester A with 2-methyl propene to create compound B;

(b) reaction of B with benzaldehyde to create compound C;

(c) reaction of C with benzyl bromide to create compound 3*.

In a particular embodiment, the method further comprises one or more of the following steps:

(a) reduction of compound 2, particularly with diisobutylaluminium hydride (DiBAl-H) to create compound D;

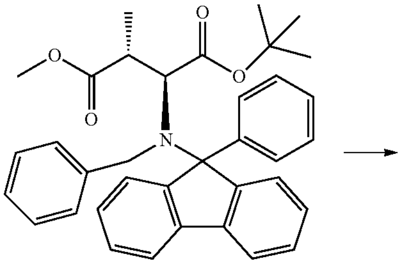

2

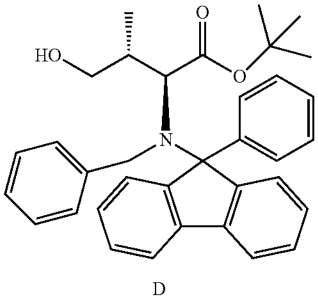

D (b) oxidation of hydroxy compound D, particularly using a Swern oxidation, to create compound E;

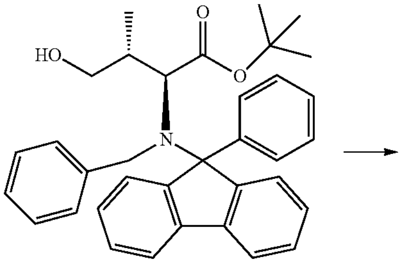

D

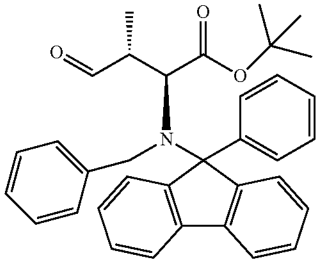

E (c) conversion of E, particularly under conditions of a Wittig reaction, to create compound 4;

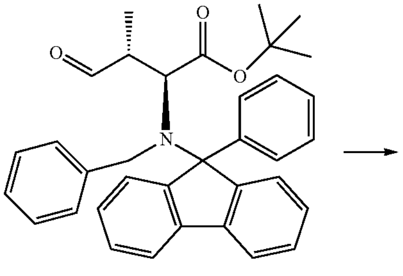

E

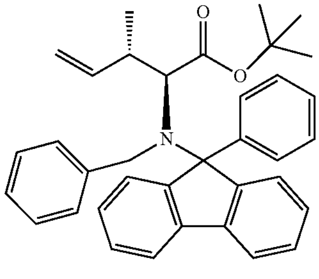

4

(d) conversion of 4, particularly under conditions of a Sharpless oxidation, to create compound F;

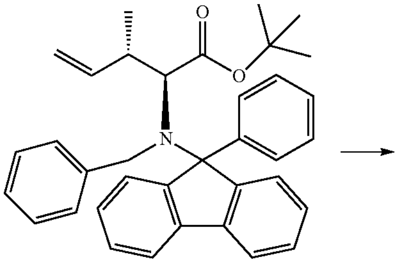

4

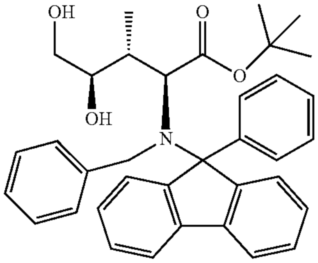

F (e) conversion of F, particularly under catalytic esterification conditions, to create compound 5;

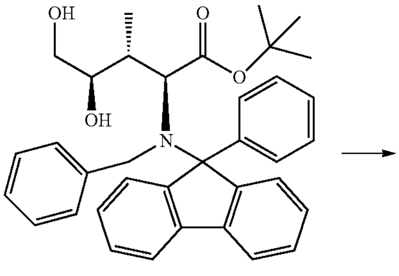

F

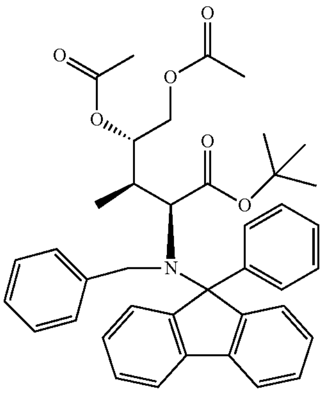

5 and (f) N-deprotection of 5, particularly using palladium-catalyzed hydrogenation, to create compound 6.

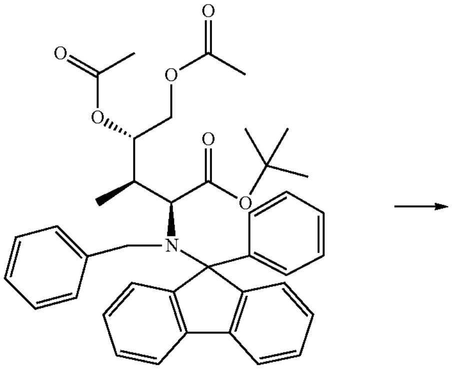

5

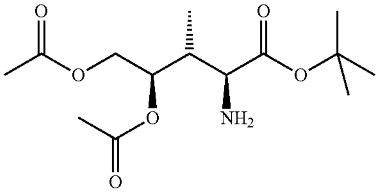

6

In a particular embodiment of the alternative aspect, the method further comprises one or more of the following steps:

(a) reduction of compound 2*, particularly with diisobutylaluminium hydride (DiBAI-H) to create compound D* (having a second benzyl protection group at the nitrogen atom instead of the phenyl fluorenyl group in compound D);

(b) oxidation of hydroxy compound D*, particularly using a Swern oxidation, to create compound E* (having a second benzyl protection group at the nitrogen atom instead of the phenyl fluorenyl group in compound E);

(c) conversion of E*, particularly under conditions of a Wittig reaction, to create compound 4* (having a second benzyl protection group at the nitrogen atom instead of the phenyl fluorenyl group in compound 4);

(d) conversion of 4*, particularly under conditions of a Sharpless oxidation, to create compound F* (having a second benzyl protection group at the nitrogen atom instead of the phenyl fluorenyl group in compound F);

(e) conversion of F*, particularly under catalytic esterification conditions, to create compound 5* (having a second benzyl protection group at the nitrogen atom instead of the phenyl fluorenyl group in compound 5);

and (f) N-deprotection of 5*, particularly using palladium-catalyzed hydrogenation, to create compound 6.

In a particular embodiment, the method further comprises the step of isolating and purifying compound 6. In a particular embodiment, compound 6 is purified using precipitation as hydrochloride and/or chromatographic purification.

In a second aspect, the present invention relates to compound 6.

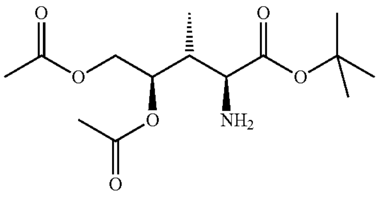

6

In a particular embodiment, compound 6 has a purity greater than 90%, particularly greater than 95%.

In the context of the present invention, the term "purity" refers to the total amount of compound 6 and of its diastereoisomers being present. A purity of greater than 90%, for example, means that in 1 g of a composition comprising compound 6, there are more than 90%, i.e. more than 900 mg, of compound 6 and/or its stereoisomers. The remaining part, i.e. the impurities may include unreacted starting material and other reactants, solvents, cleavage products and/or side products.

In a particular embodiment, a composition comprising compound 6 with a purity greater than 90% comprises more than 100 mg of compound 6.

In a particular embodiment, compound 6 has a diastereomeric purity greater than 70:30.

In the context of the present invention, the term "diastereomeric purity" refers to the ratio of the amount of compound 6 being present in a composition comprising compound 6 to the amounts of its diastereoisomers being present in said composition. A diastereomeric purity of greater than 70:30, for example, means that more than 70% of the total amount of protected dihydroxyisoleucines in a composition comprising compound 6 and of its diastereomers is compound 6, whereas the total amount of all diastereoisomers of compound 6 is correspondingly less than 30%.

In a particular embodiment, a composition comprising compound 6 with a diastereomeric purity greater than 70:30 comprises more than 100 mg of compound 6.

In a third aspect, the present invention relates to a kit comprising compound 6, particularly a kit comprising at least 100 mg of compound 6,and at least one additional reagent for the synthesis of amatoxins or precursors thereof.

In particular embodiments, compound 6 in the kit has a purity greater than 90%, particularly greater than 95%, and/or a diastereomeric purity greater than 70:30.

In particular embodiments, said at least one additional reagent is selected from the list of:

(i) a resin, particularly a resin selected from the group of: a Merrifield resin; a Rink-Amid resin; and a THP-resin;

(ii) a protected hydroxyproline, particularly fluorenylmethyloxycarbonyl-(Fmoc-)-protected O-allyl hydroxyproline (FmocHypOAll);

(iii) a protected asparagine, particularly Fmoc-protected N-trityl asparagine (Fmoc(N-Tri)AsnOH);

(iv) a protected Cys-Trp dipeptide, particularly Fmoc-protected Cys-Trp dipeptide with —SH and —OH protection groups (FmocCys(S-2-((o-$NO_2$Ph)$SO_2$Trp-O-Allyl))]OH);

(v) a protected glycine, particularly Fmoc-protected glycine (FmocGly);

(vi) a protected isoleucine, particularly Fmoc-protected isoleucine (FmocIle);

(vii) a peptide coupling reagent, particularly a peptide coupling reagent selected from the group of: O-(benzotriazol-1-yl)-N,N,N',N'-tetramethyluronium tetrafluoroborate (TBTU); benzotriazol-1-yl-oxytripyrrolidinophosphonium hexafluorophosphate (PyBOP); and o-(7-azabenzotriazol-1-yl)-N,N,N',N'-tetramethyluronium hexafluorophosphate (HATU); and (viii) a tertiary amine, particularly N,N-diisopropylethylamine (DiPEA).

In yet another aspect, the present invention relates to a method for synthesizing an amatoxin, or precursor molecule therefor, comprising the step of (a) coupling compound 6 to hydroxyproline, particularly by reacting compound 6 with a hydroxyproline-preloaded resin, particularly by coupling compound 6 to the free C-terminus of FmocHypOH immobilized on a resin L, for example a tetrahydropyranyl (THP) resin.

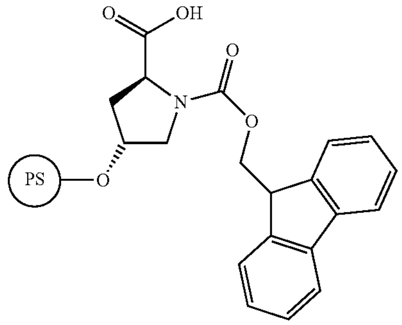

L

+

6

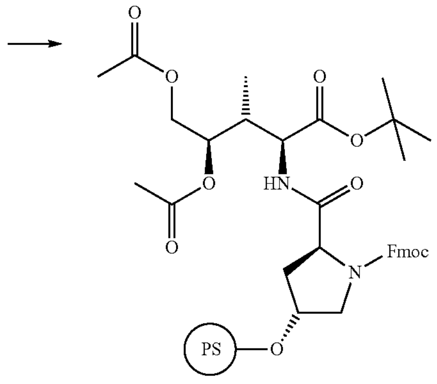

6

In particular embodiments, the remaining amino acids are then coupled by a N-terminal synthetic strategy. In particular such embodiments, the method of the present invention additionally comprises one or more of the following steps:

(b) iterative Fmoc N-deprotection and coupling of G with Fmoc-(N-Tri)Asn OH; FmocCys(S-2-((o-$NO_2$Ph)$SO_2$Trp-O-Allyl))]OH, Fmoc-Gly OH, Fmoc-Ile OH, Fmoc-Gly OH to create compound H:

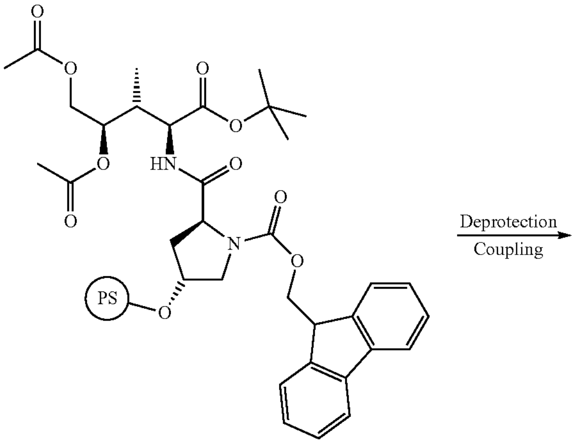

G

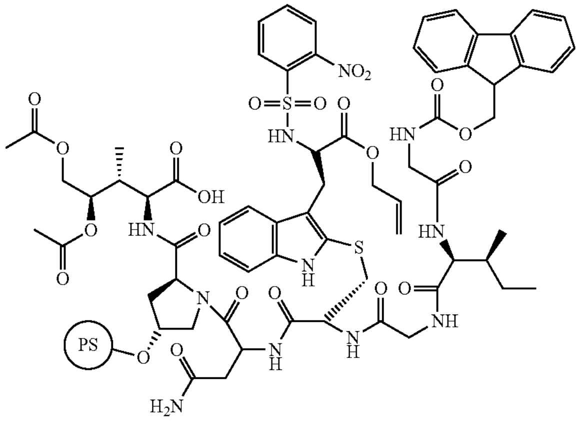

H (c) O-allyl- and N-Fmoc deprotection of H followed by cyclisation to create compound I (B-ring closure):

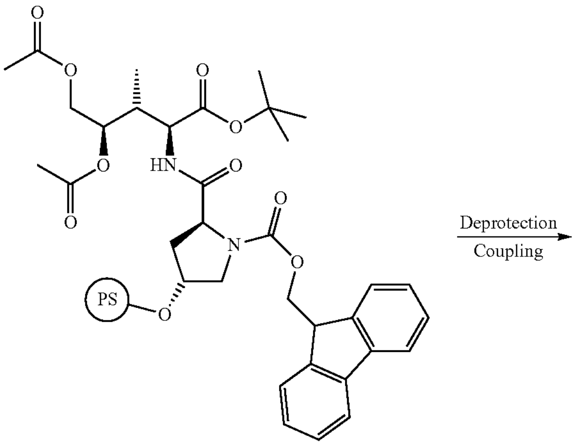

H

-continued
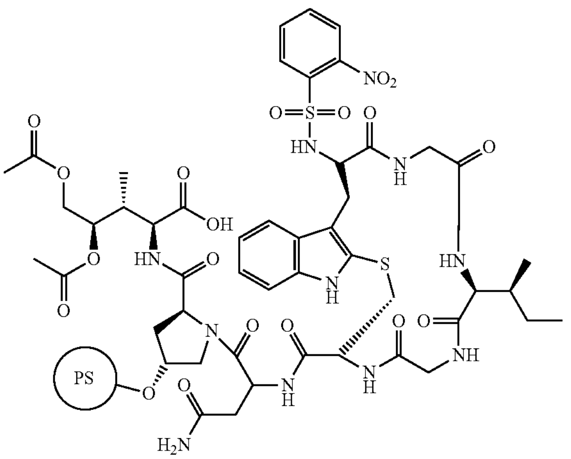
I
(d) 2-nitro aryl sulfonamide N-deprotection and secession of I from resin to create compound J:
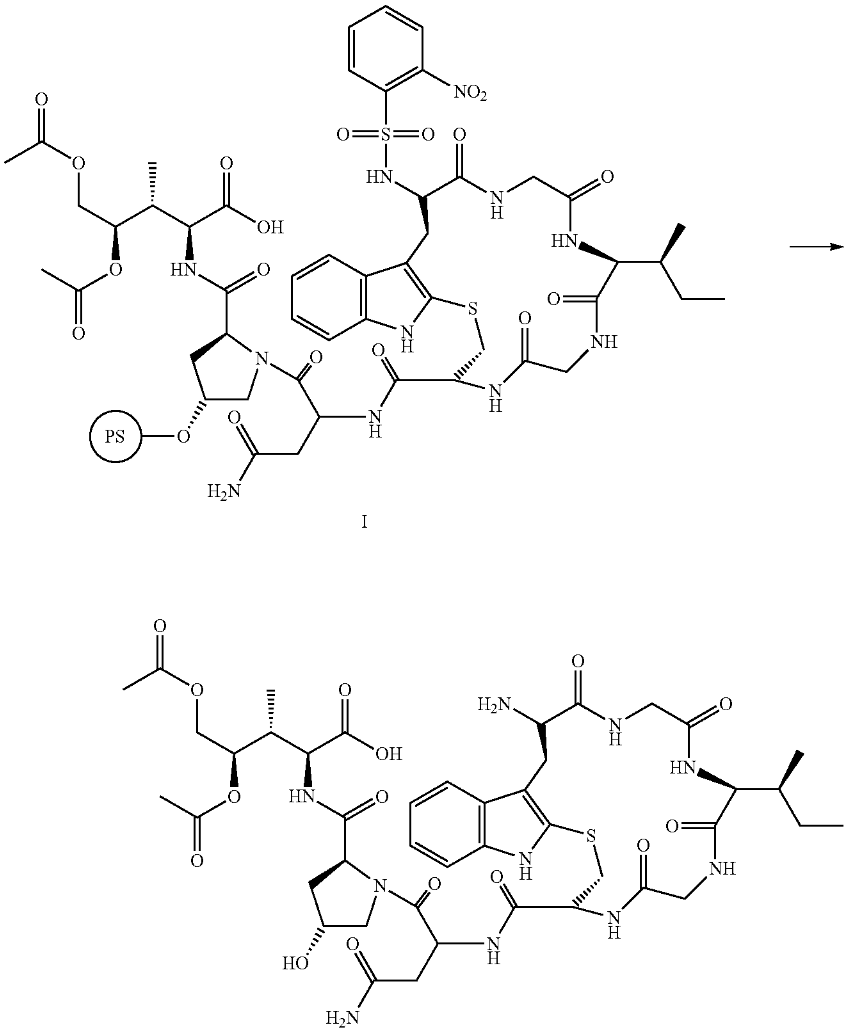
I
J (e) solution phase cyclisation of J creating Amanitin derivative K:

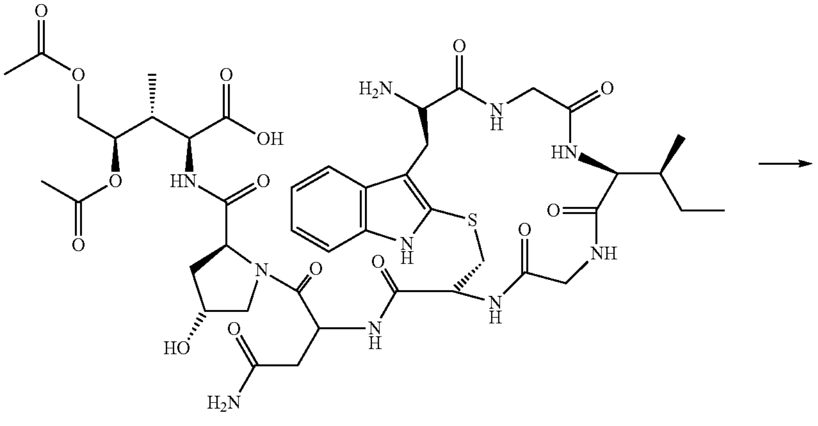

J

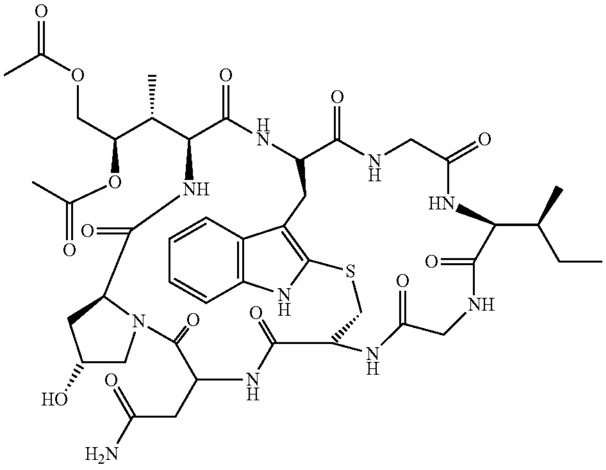

K

In yet another aspect, the present invention relates to a method for synthesizing an amatoxin, or precursor molecule therefor, in solution.

In certain embodiments, such method comprises one or more of the following steps:

(a) coupling compound 6 to hydroxyproline, particularly by reacting compound 6 with a hydroxyproline, particularly by coupling compound 6 to the free C-terminus of Fmoc (O$^t$Bu) HypOH;

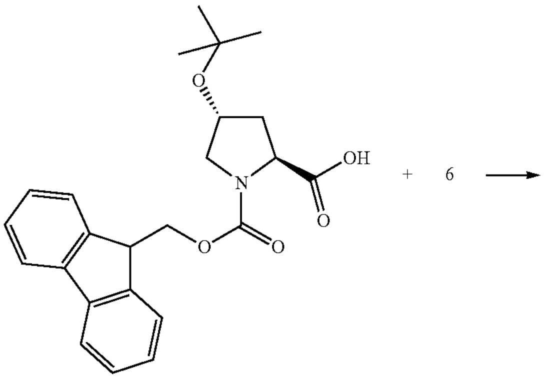

L

-continued

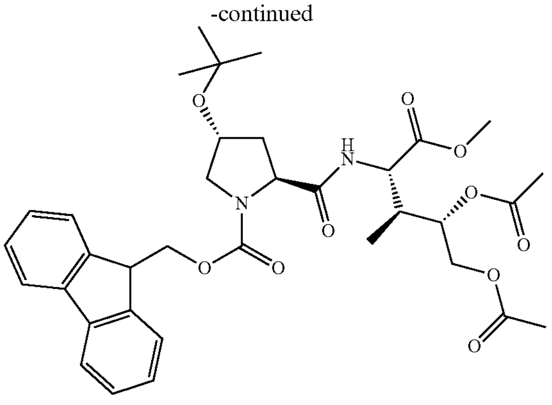

M (b) iterative Fmoc N-deprotection and coupling of M with Fmoc-(N-Tri)Asn OH; Fmoc-(S-Tri)Cys OH, Fmoc-Gly OH, Fmoc-Ile OH, Fmoc-Gly OH and N-Boc-HPI OH to create compound N;

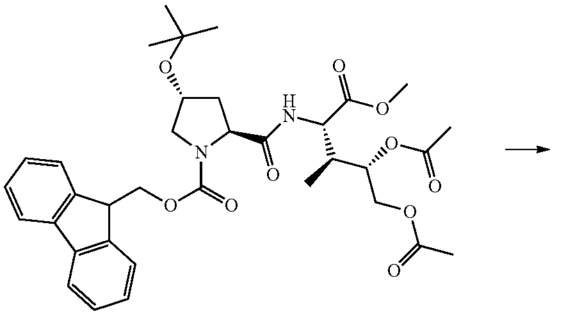

M

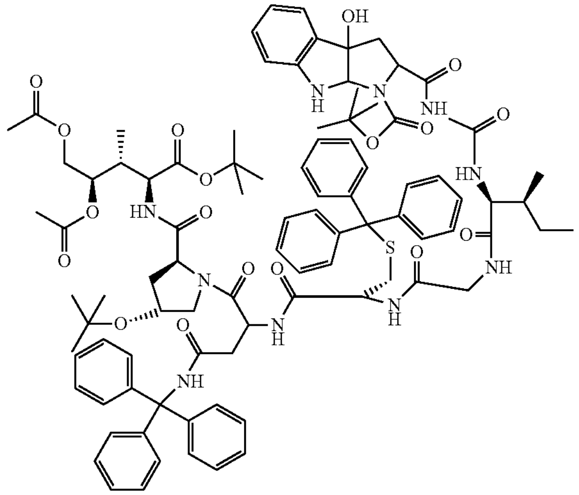

N (c) acidic deprotection of N- and S-trityl, O-tert-butyl and N-tertbutyloxycarbonyl protection groups and in situ ring closure by a Savige-Fontana reaction (Savige & Fontana, Int J Pept Protein Res. 15 (1980) 102-12) yielding compound J.

In yet another aspect, the present invention relates to a method for synthesizing an amatoxin, or precursor molecule therefor, in solution, comprising the step of coupling compound 6 to hydroxyproline, particularly by reacting compound 6 with a hydroxyproline, particularly by coupling compound 6 to the free C-terminus of Fmoc (O$^t$Bu) HypOH.

In particular embodiments, the amatoxin is an amatoxin with a dihydroxyisoleucine moiety as amino acid 3 (see FIG. 1).

In the context of the present invention, the term "amatoxin" includes all cyclic peptides composed of 8 amino acids as isolated from the genus Amanita and described in Wieland, T. and Faulstich H. (Wieland T, Faulstich H., CRC Crit Rev Biochem. 1978 December; 5(3):185-260), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in which the thioether sulfoxide moiety is replaced by a sulfide, sulfone, or by atoms different from sulfur, e.g. a carbon atom as in a carbaanalogue of amanitin, in each case wherein any such derivative or analogue is functionally active by inhibiting mammalian RNA polymerase II.

Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or target-binding moieties as defined above. Amatoxins which are particularly suitable for the conjugates of the present invention are α-amanitin, β-amanitin, γ-amanitin, ε-amanitin, amanin, amaninamide, amanullin, and amanullinic acid as shown in FIG. 1 as well as salts, chemical derivatives, semisynthetic analogues, and synthetic analogues thereof. Particularly preferred amatoxins for use in the present invention are α-amanitin, β-amanitin, and amaninamide.

As used herein, a "chemical derivative" (or short: a "derivative") of a compound refers to a species having a chemical structure that is similar to the compound, yet containing at least one chemical group not present in the compound and/or deficient of at least one chemical group that is present in the compound. The compound to which the derivative is compared is known as the "parent" compound. Typically, a "derivative" may be produced from the parent compound in one or more chemical reaction steps.

EXAMPLES

In the following, the invention is explained in more detail by non-limiting examples:

Example 1

Mannich Reaction Using Propionic Aldehyde and N-PMP Glyoxalimine

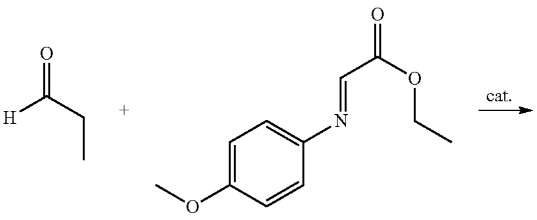

-continued

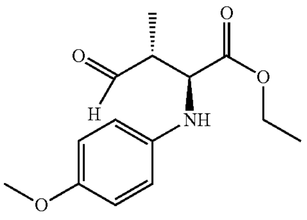

One of the key structural features of 1 is the 2S,3R conformation of the amino and methyl group. An easy access for the construction of the adjacent stereocenters is the Mannich reaction. However both stereocenters presume an anti-Mannich type reaction with high diastereo- and enantiocontrol. This premise is described by use of a designed organocatalyst readily described in J. Am. Chem. Soc., 2006, 128, 1040-1041. However, different approaches to remove the PMP-group failed and gave reaction mixtures, so that this approach was finally discarded. It is known in literature that removal can be quite tedious and unsuccessful, though the PMP-group is necessary for the reaction.

Example 2

Alkylation of Aspartic Acid Derivative 2.1 Introduction

An alternative approach for synthesizing a γ,δ-dihydroxyisoleucine synthon with correct stereo configuration (2S,3R,4R) started with aspartic acid derivative 3. Similar approaches have been described in the literature (see Yoshida et al., A large scale production of (3S,4S)-3-(tert-Butoxycarbonyl)amino-4-methylpyrrolidine and its analogs from L-Aspartic acid, Chem Pharm Bull (1996), 44, 1128-1131; Wolf and Rapoport, Conformationally constrained Peptides. Chirospecific Synthesis of 4-Alkyl-Substituted g-Lactam-Bridged Dipeptides from L-Aspartic Acid', J Org Chem (1989), 54, 3164-3173). It turned out that is was critically important to (i) use a combination of either (ia) a benzyl and a phenyl fluorenyl group, or (ib) two benzyl groups, for protecting the free amino group, and (ii) to use Lithium hexamethyldisilazane (LHMDS) instead of the corresponding potassium salt. Potassium hexamethyldisilazane (KHMDS) led to the opposite configuration.

2.2 Synthesis of Compound 2

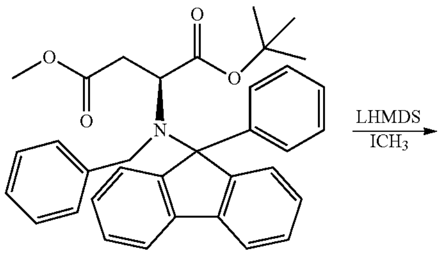

3

-continued

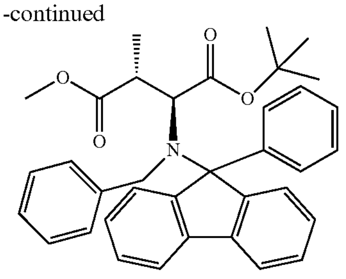

2

A three necked round bottom flask with magnetic stirring bar, dropping funnel and low temperature thermometer was charged with 16.3 mmol, 8.7 g of compound 3 (see Example 3), dissolved in 150 ml dry tetrahydrofuran, and cooled to −20° C. Lithium hexamethyl disilazide, 40 ml of a 1.0 M solution in Hexane was added drop wise within 15 minutes. The reaction was kept at −20° C. for 2 hours before cooling to −80° C. Finally 12.2 ml, 19,6 mmol, 1.2 eq. methyl iodide was added. The reaction was allowed to warm slowly and kept for further 4 hours at −20° C. The reaction was finally quenched by addition of 10 ml methanol, allowed to warm to room temperature and poured into 150 ml water. The aqueous phase was extracted with t-butylmethylether, dried over $MgSO_4$ and concentrated in vacuum. Crude product: 9.0 g. 1H-NMR of crude product revealed a diastereoselective purity of better than 5:1. Yield 7.2 g, 81%.

The crude product was purified by flash chromatography, 330 g Silica, n-hexane/t-butylmethyl ether gradient from 0% to 50%.

$^1$H-NMR: d 0.72 (d, 3 H, J=5.6 Hz), 1.03 (s, 9 H), 2.64 (dt, 1 H, J=5.6, 8.4 Hz), 3.55 (s, 3 H), 3.85 (d, 1 H, J=8.4 Hz), 4.31 (d, 1 H, J=11.2 Hz), 4.65 (d, 1 H, J=11.2 Hz), 7.15-7.94 (m, 18 H).

2.3 Synthesis of Compound 2*

Analogous to Example 2.2, compound 2* can be synthesized from 3*.

Example 3

Synthesis of Compound 3

3.1 Introduction

Compound 3 was synthesized in accordance with the protocol described by Dunn et al. (Dunn et al., Stereoselective synthesis of 2,3-diamino acids. 2,3-Diamino-4-phenylbutanoic acid, J. Org. Chem. 55 (1990) 5017-25.

3.2 Synthesis of Compound B

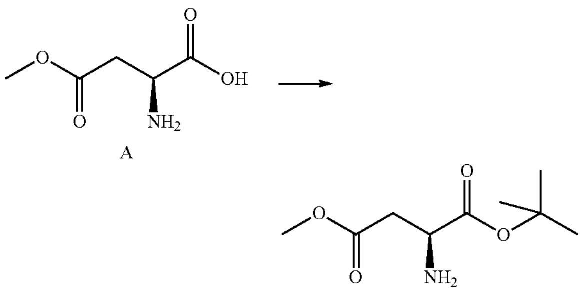

A

B

In a round-bottomed glass cylinder with screw cap and stirring bar was placed 25 g, 136 mmol 4-methyl-L-aspartate hydrochloride. The mono ester A was suspended in 100 ml dioxane/tetrahydrofuran (1:1, v/v) and 25 ml of sulfuric acid and cooled to −30° C. (cryostat). 2-methylpropene, 200 g, 3.56 mol, was condensed into. The cylinder was closed and allowed to warm to room temperature. The reaction mixture was poured onto 1000 ml saturated sodium bicarbonate solution and extracted with ethyl acetate (5 times 400 ml). The combined organic phase was dried over $MgSO_4$ and concentrated in vacuum. Yield: 17.88 g, 64.6%.

3.3 Synthesis of Compound C

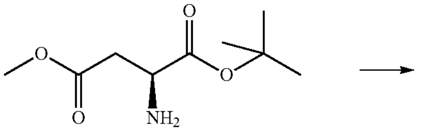

B

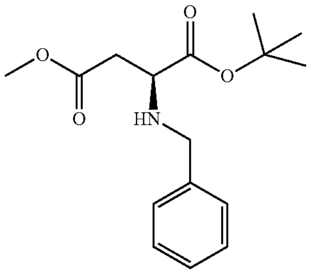

C

A round-bottomed flask with thermometer and stirring bar was charged with B, 17.9 g, 87.9 mmol, dissolved in 500 ml methanol and 150 ml acetic acid. Benzaldehyde, 16.0 ml, 158 mmol, was added dropwise. The reaction was kept at room temperature for 2 hours and finally cooled to 0° C. Sodium cyano borohydride, 10.0 g, 159 mmol was added within 45 min and stirred for further 15 min at 0° C. The reaction mixture was finally poured into 1000 ml sodium bicarbonate and stirred for 10 minutes. After dichloromethane extraction (5 times 250 ml) the combined organic phases were dried over $MgSO_4$ and concentrated in vacuum. Crude product: 35 g. Yield 14.3 g, 55.4%.

Flash chromatographic purification, 330 g $SiO_2$, n-hexane/ethylacetate gradient 0 to 50%.

$^1$H-NMR: d 1.42 (s, 9 H), 2.29 (s, 1 H), 2.62 (t, 2 H, J=9.2 Hz), 2.50 (t, 1 H, J=8 Hz), 3.62 (s, 3 H), 3.67 (d, 1 H, 17.6 Hz), 3.83 (d, 1 H, J=17.2 Hz), 7.19-7.30 (m, 5 H).

3.4 Synthesis of Compound 3

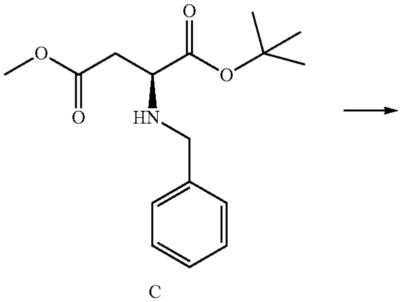

C

-continued

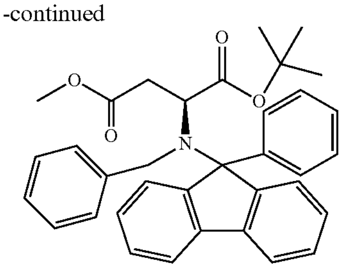

3

A round-bottomed flask with stirring bar was charged with C, 21.3 g, 51.6 mmol, in 500 ml acetonitrile. 9-bromo-9-phenyl fluorene, 25.0 g, 77.8 mmol, 20.0 g, 60.3 mmol lead nitrate, 31.7 g, 149.3 mmol $K_3PO_4$ were added. The reaction mixture was kept at room temperature for 2.0 h. After completion, the reaction was diluted with 500 ml dichloromethane, dried over $Na_2SO_4$ and filtered over Celite. The product was concentrated in vacuum. Yield: 16.2 g, 41.7%.

Flash chromatographic purification, 330 g $SiO_2$, n-hexane/t-butylmethylether, gradient 0 to 50%.

$^1$H-NMR: d 1.14 (s, 9 H), 1.92 (dd, 1 H, J=2.8, 16 Hz), 2.54 (dd, 1 H, 10.8, 15.8 Hz), 3.40 (s, 3 H), 3.86 (d, 1 H, J=13.6 Hz), 4.21 (d, 1 H, J=14 Hz), 7.17-7.83 (m, 18 H).

Example 4

Synthesis of Compound 6

4.1 Synthesis of Compound D

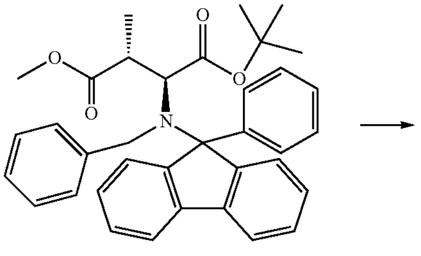

2

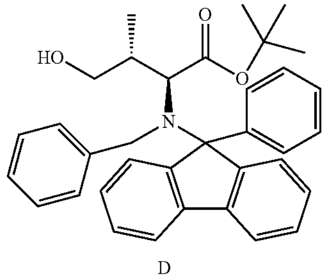

D

A round bottom flask equipped with stirring bar, thermometer and dropping funnel was charged with 2, 16.4 g, 29.9 mmol dissolved in 150 ml dry tetrahydrofuran and cooled to −30° C. A 1.0 M solution (150 ml) diisobutyl aluminium hydride was added under an inert atmosphere (argon) within 1.0 hour and stirred for additional 16 hours. The reaction was hydrolysed with $Na_2SO_4$ decahydrate and allowed to warm to room temperature. The precipitation was filtered off and washed extensively with t-butylmethylether. The organic phase was concentrated in vacuum. Yield: 14.3 g, 92%.

Flash chromatographic purification, 330 g $SiO_2$, n-hexane/ethylacetate gradient 0 to 50%.

$^1$H-NMR: d 0.45 (d, 3 H, J=6.8 Hz), 1.02 (s, 9 H), 3.09 (d, 1 H, J=10.8 Hz), 3.34 (dq, 1 H, J=7.2 Hz, J=14.8 Hz), 4.00 (d, 2 H, J=10.8 Hz), 4.36 (d, 1 H, 13.6 Hz), 4.73 (d, 1 H, J=13.6 Hz), 7.20-7.76 (m, 18 H).

4.2 Synthesis of Compound E

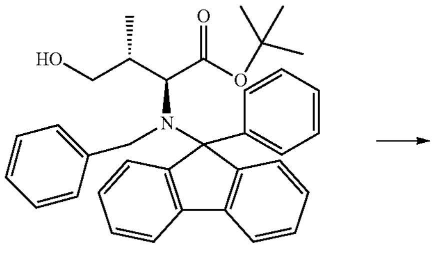

D

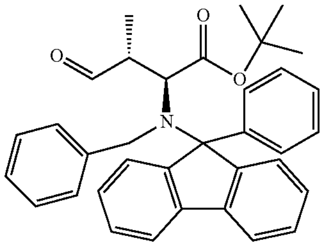

E

A round bottom flask equipped with stirring bar, thermometer, dropping funnel and argon inlet was charged with oxalylchloride 3.28 ml, 35.5 mmol in dichloromethane and cooled to −80° C. Dry dimethylsulfoxide 5.47 ml, 71.1 mmol diluted with 20 ml dichloromethane was slowly added. Compound D 13.67 g, 25.9 mmol, dissolved in 30 ml dichloromethane, was added over a period of 15 minutes. After additional 15 min at −80° C., triethylamine was added and the reaction allowed to warm to room temperature. Both layers were separated and the aqueous extracted with dichloromethane (4 times 150 ml). The combined organic phases were dried over $MgSO_4$, and concentrated in vacuum. Crude product: 16.9 g. The crude product was directly converted to the olefin.

4.3 Synthesis of Compound 4

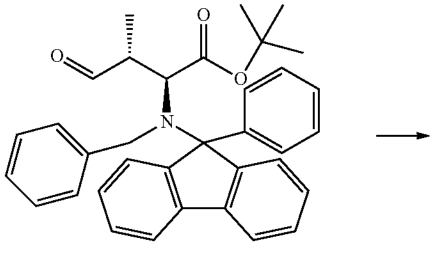

E

-continued

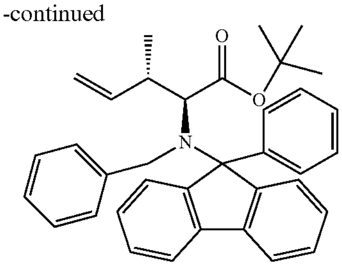

4

A round bottom flask with stirring bar, thermometer and argon inlet was charged with Sodium hydride 2.32 g, 57.9 mmol suspended in 120 ml dimethylsulfoxide. The suspension was warmed to 50° C. for 30 minutes and cooled to room temperature. Solid methyltriphenyl phosphonium bromide was added then and stirred for 15 minutes. The crude product E, dissolved in 20 ml dimethylsulfoxide was added and stirred for additional 16 hours. After hydrolyses (300 ml water), ethyl acetate extraction (4 times 150 ml), extensive washing of the combined organic phase with water (3 times 150 ml) and brine, the solution was dried with $MgSO_4$ and concentrated in vacuum. Yield: 13.3 g, 99.2% (2 steps).

Flash chromatographic purification, 330 g $SiO_2$, n-hexane/ethylacetate gradient 0 to 80%.

$^1$H-NMR: d 0.51 (d, 3 H, J=1.6 Hz), 1.05 (s, 9 H), 2.14 (hept, 1 H, J=0.8 Hz), 3.15 (d, 1 H, 10.8 Hz), 4.30 (d, 1 H, J=14 Hz), 4.49 (dd, 1 H, J=1.2, 17.6 Hz), 4.57 (d, 1 H, 13.6 Hz), 5.03 (d, 1 H, J=0.8, 10.8 Hz), 5.95 (m, 1 H), 7.26-7.60 (m, 18 H).

4.4 Synthesis of Compound F

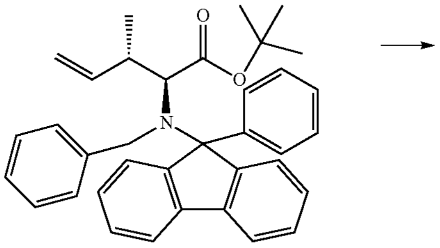

4

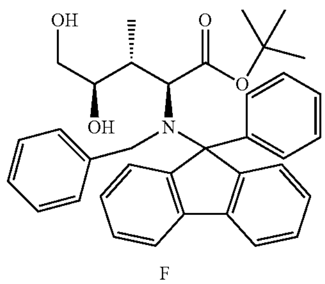

F

A round-bottomed flask was charged with 100 g AD-mix (beta, commercial source) and dissolved in 60 ml t-butanol/water (1:1, v/v). Compound 5, 3.75 g, 7.3 mmol, dissolved in 17 ml dioxane was added in one portion. The reaction was stirred at room temperature for 4 days until completion of the reaction. The reaction was quenched by addition of $Na_2SO_3$ and extracted with ethyl acetate (4 times 50 ml), washed with saturated $NH_4Cl$ and brine, dried over $MgSO_4$ and concentrated in vacuum. Yield: 1.19 g, 29%.

Flash chromatographic purification, 330 g $SiO_2$, dichloromethane/t-butyl methyl ether gradient 0 to 80%.

$^1$H-NMR: d 0.38 (D, 3 H, J=6.8 Hz), 1.03 (s, 9 H), 1.84 (s+m, 2 H, J=8.8 Hz), 3.24 (dd, 1 H, J=4.8, 11.4 Hz), 3.38 (d, 2 H, J=10.9 Hz), 3.76 (m, 1 H), 4.40 (d, 1 H, J=13.3 Hz), 4.95 (d, 1 H, J=13.3 Hz), 5.55 (s, 1 H), 7.26-7.91 (m, 18 H).

4.4 Synthesis of Compound 5

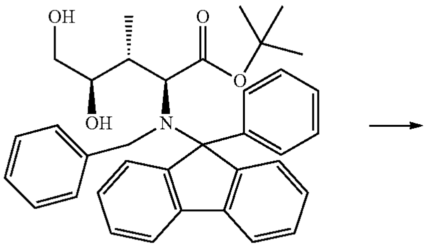

F

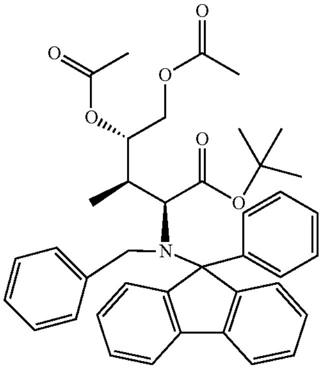

5

A round-bottomed flask with magnetic stirring bar was charged with F, 2.1 g, 3.64 mmol, dissolved in 75 ml dichloromethane. Excess acetic acid anhydride, 5.0 ml, 52.3 mmol and catalytic quantities of dimethylaminopyridine were added. The reaction was allowed to stir at room temperature overnight. Yield: 1.83 g, 81%.

Flash chromatographic purification, 330 g $SiO_2$, hexane/t-butylmethyl ether gradient 0 to 20%.

$^1$H-NMR: d 0.49 (d, 3 H, J=7.2 Hz), 1.05 (s, 9 H), 1.74 (m, 1 H, J=2.90 Hz), 1.88 (s, 3 H), 2.11 (s, 3 H), 3.18 (d, 1 H, J=10.5 Hz), 3.60 (dd, 1 H, J=2.3, 12.2 Hz), 4.32 (d, 1 H, J=13.9 Hz), 4.74 (d, 1 H, J=13.9 Hz), 5.98 (dd, 1 H, J=2.4, 84 Hz), 7.10-7.73 (m, 18 H).

4.4 Synthesis of Compound 6

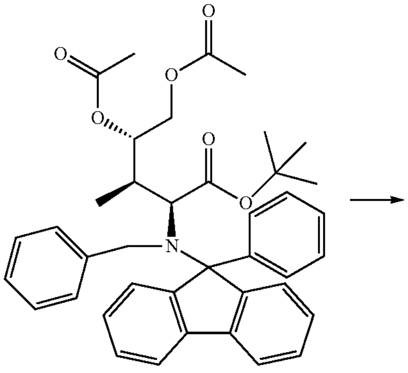

5

-continued

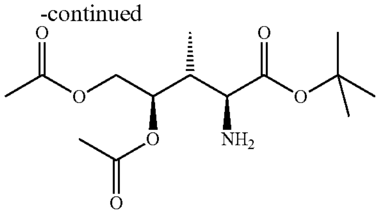

6

A round-bottomed flask equipped with an argon inlet and vacuum manifold was charged with 5, 2.0 g, 3.1 mmol dissolved in 50 ml 0.1M hydrochloric acid in ethanol and 200 mg 10% Palladium on charcoal. After flushing the flask with hydrogen, the reaction was allowed to stir for 16 hours at room temperature. The flak was flushed with Argon, filtered and the filtrate concentrated in vacuum. The clear oil was treated with n-hexane (3 times) to get rid of phenylfluorene. A hydrochloric salt of 6 was obtained as white solid. Yield: 0.92 g, 98%.

Purification by precipitation or chromatography.

$^1$H-NMR: (major isomer) d 1.16 (d, 3 H, J=6.8 Hz), 1.47 (S, 9 H), 2.06 (s, 3 H), 2.09 (s, 3 H), 2.78 (m, 1 H, J=7.7 Hz), 4.04 (dd, 1 H, J=3.9, 12.5 Hz), 4.15 (s, 1 H), 4.52 (dd, 2 H, J=2.08, 12.6 Hz), 5.02 (m, 2 H), 8.86 (s, 2 H).

$^{13}$C-NMR: (major isomer) d 11.5, 20.8, 21.7, 35.0, 53.9, 62.4, 72.2, 84.9, 166.2, 169.9, 170.7.

Example 5

Synthesis of α-Amatoxin 5.1 Synthesis of Compound G

An open vessel polypropylene reaction tube equipped with a frit and drain valve was charged with 0.5 g, 0.5 mmol FmocHypOH tetrahydropyranyl polystyrene and allowed to swell in 3.0 ml dimethylformamide for 20 minutes. After removal of solvent through the drain valve, the reaction vessel was charged with 179 mg, 0.6 mmol of 6, dissolved in 1.5 ml dimethylformamide, 1.5 ml of a 1 mM solution of hydroxybenzothiazole in dimethylformamide, 1.5 ml of a 1 mM solution of (benzotriazol-1-yloxy)tripyrrolidinophosphonium hexafluorophosphate in dimethylformamide and 259 μl of diisoppropylethylamine. After homogenisation with a glass bar the reaction was heated microwave assisted to 70° C. for 4.0 minutes and finally washed with dimethylformamide (3 times) and dichloromethane (2 times).

An aliquot, approx. 20 mg of the polymer was cleaved off with trifluoroacetic acid/water/triethylsilane (8:2:10; v/v/v) for mass spectroscopic analysis.

MS: 582.92; $[M-{}^tBu+H]^+$; Fmoc-Hyp-bis(O-acetyl)dihydroxy-Ile-O$^t$Bu 5.2 Synthesis of Compound H Compound G was then iteratively Fmoc deprotected and coupled with the remaining 6 amino acids as follows:

Fmoc-N-Deprotection:

The resin was twice treated with 4.5 ml of a 20% piperidine solution in dimethylformamide and heated to 70° C. for 3 minutes microwave assisted. The resin was then washed with dimethylformamide (3 times).

Amino Acid Coupling:

Deprotected resin bound peptide in 1.5 ml dimethylformamide was successively reacted with amino acids (see list) dissolved in 1.5 ml dimethylformamide, 1.5 ml of a 1 mM solution of hydroxybenzothiazole in dimethylformamide, 1.5 ml of a 1 mM solution of (benzotriazol-1-yloxy)tripyrrolidinophosphonium hexafluorophosphate in dimethylformamide and 259 μl of diisopropylethylamine. After homogenisation with a glass bar the reaction was heated microwave assisted to 70° C. for 4.0 minutes and finally washed with dimethylformamide (3 times) and dichloromethane (2 times).

An aliquot, approx. 20 mg of the polymer was cleaved off with trifluoroacetic acid/water/triethylsilane (8:2:10; v/v/v) for mass spectroscopic analysis.

Amino Acids to be Coupled:

1. Fmoc-(N-Tri)Asn OH
2. Fmoc-Cys(S-2-((o-$NO_2$Ph)$SO_2$Trp-O-Allyl))]OH
3. Fmoc-Gly OH
4. Fmoc-Ile OH
5. Fmoc-Gly OH MS: 1227.14; [M−$^t$Bu+H]$^+$; 1283.00; [M+H]$^+$; FmocCys (S-2-((o-$NO_2$Ph)$SO_2$Trp-O-Allyl))]-Asn-Hyp-bis(O-acetyl) dihydroxy-Ile-O$^t$Bu.

MS: 1453.98; [M−$^t$Bu+H]$^+$; [M+H]$^+$; FmocGly-Ile-Gly-Cys(S-2-((o-$NO_2$Ph)$SO_2$Trp-O-Allyl))]-Asn-Hyp-bis(O-acetyl)dihydroxy-Ile-O$^t$Bu 5.3 Synthesis of Compound I; B-Ring Closure Resin H was successively allyl- and Fmoc-deprotected before B-ring cyclisation:

Allyl-O-Deprotection

The resin was shaken over night at room temperature with 874 mg, 5.6 mmol N,N-dimethylbarbituric acid, 258 mg, 0.224 mmol $Pd(PPh_3)_4$ in dichloromethane. After 16 hours the resin was washed with dichloromethane; dimethylformamide; acetonitrile; and t-butylmethyl ether.

Fmoc-N-Deprotection:

The resin was twice treated with 4.5 ml of a 20% piperidine solution in dimethylformamide and heated to 70° C. for 3 minutes microwave assisted. The resin was then washed with dimethylformamide (3 times).

B-Ring Formation

Deprotected resin bound peptide in 3.0 ml dimethylformamide was reacted with 1.5 ml of a 1 mM solution of hydroxybenzothiazole in dimethylformamide, 1.5 ml of a 1 mM solution of (benzotriazol-1-yloxy)tripyrrolidinophosphonium hexafluorophosphate in dimethylformamide and 259 μl of diisopropylethylamine. After homogenisation with a glass bar the reaction was heated microwave assisted to 70° C. for 4.0 minutes and finally washed with dimethylformamide (3 times) and dichloromethane (2 times).

An aliquot, approx. 20 mg of the polymer was cleaved off with trifluoroacetic acid/water/triethylsilane (8:2:10; v/v/v) for mass spectroscopic analysis.

MS: 1174.08; [M−$^t$Bu+H]$^+$; 1229.96; [M+H]$^+$; [Gly-Ile-Gly-Cys(S-2-((o-$NO_2$Ph)$SO_2$Trp))]ring-Asn-Hyp-bis(O-acetyl)dihydroxy-Ile-O$^t$Bu 5.4 2-$NO_2$-Phenylsulfonyl-N-Deprotection and Resin Secession, Compound J Resin I was 2-$NO_2$-phenylsulfonyl-deprotected and finally cleaved from resin 2-$NO_2$-Phenylsulfonyl-N-Deprotection:

The resin was repeatedly (3 times) treated with 500 μl mercaptoethanol and 500 μl diazabicycloundecene in 4 ml dimethylformamide for 2 hours. The resin was then washed intensely with dimethylfomamide, dichloromethane, acetonitrile and t-butylmethylether.

Resin Secession:

The resin was then treated with 6 ml of trifluoroacetic acid/water/triethylsilane (8:2:10; v/v/v) at room temperature over night and the crude protein concentrated in vacuum.

MS: 989.18; [M−$^t$Bu+H]$^+$; [Gly-Ile-Gly-Cys(S-2-(Trp))] ring-Asn-Hyp-bis(O-acetyl)dihydroxy-Ile-O$^t$Bu 5.5 Synthesis of Compound K; A-Ring Formation In a reaction flask with stirring bar crude product J was dissolved in 25 ml dimethylformamide. To the solution was added 85 μl, 2.5 mmol diisopropylethylamine and 135 μl, 2.5 mmol diphenylphsophazide. The reaction mixture was allowed to stir over night at room temperature. The solution was finally concentrated in vacuum, dissolved in 0.5 ml Methanol and purified. Yield: 4.9 mg The crude reaction mixture was purified by preparative column chromatography.

MS: 858.94; [M+H]$^+$

Example 6

Synthesis of Compound 3*

Analogous to Example 3.4, compound 3* can be synthesized from compound C by using benzyl bromide instead of 9-bromo-9-phenyl fluorene for N-protection.

Example 7

Alternative Synthesis of Compound 6

Analogous to Example 4, compound 6 can be synthesized from compound 2* via intermediate compounds D*, E*, 4*, F* and 5* (in each having a second benzyl protection group at the nitrogen atom instead of the phenyl fluorenyl group in the corresponding compound D, E, 4, F and 5, respectively).

The invention claimed is:

1. A method for the synthesis of γ, δ-dihydroxyisoleucine 1, or of a synthon for compound 1, comprising the step of methylating compound 3 or 3*, wherein the 3* has a second benzyl group at the nitrogen atom instead of the phenyl fluorenyl group in compound 3, with methyl iodide in the presence of lithium bis(trimethylsilyl)amide (LHMDS):

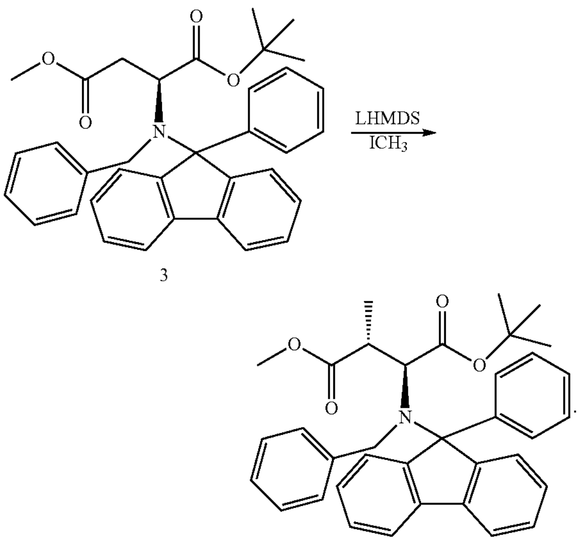

3

2

2. The method of claim 1, wherein the methylation is performed at a temperature between about −10° C. and about −80° C. in an ether for between about 12 and about 20 hours.

3. The method of claim 1, further comprising at least one of (a), (b), and (c):

(a) reaction of L-aspartic acid, monomethyl ester A with 2-methyl propene to create compound B:

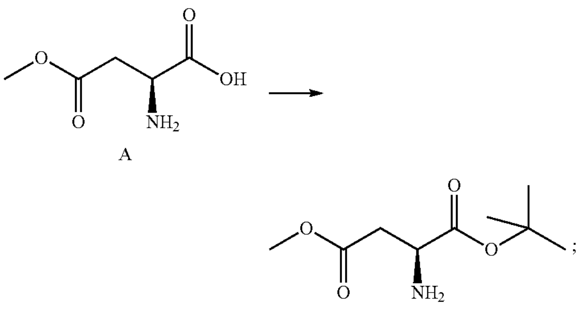

A

B (b) reaction of B with benzaldehyde to create compound C:

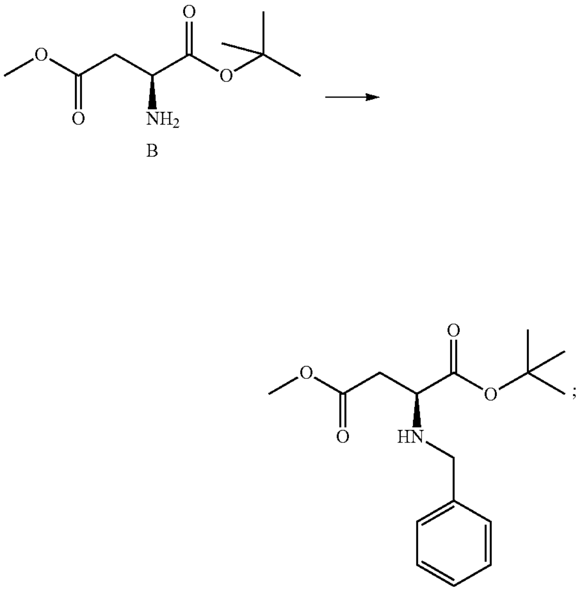

B

C (c) reaction of C with phenyl fluorenyl bromide to create compound 3, or with benzyl bromide to create compound 3*:

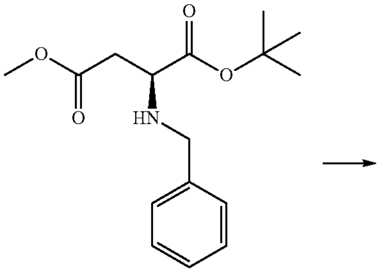

C

-continued

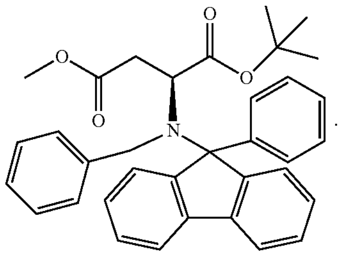

3

4. The method of claim 1, further comprising at least one of (a), (b), (c), (d), (e), and (f):

(a) reduction of compound 2 or compound 2*, wherein the 2* has a second benzyl group at the nitrogen atom instead of the phenyl fluorenyl group in compound 2, to create compound D or D*, wherein the D* has a second benzyl group at the nitrogen atom instead of the phenyl fluorenyl group in compound D, respectively:

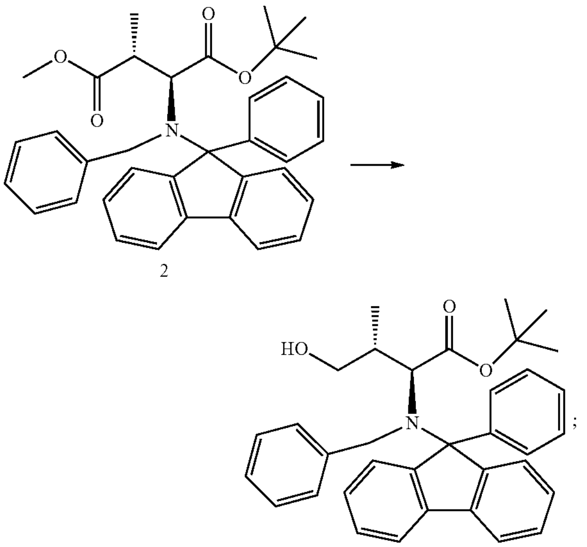

2

D (b) oxidation of hydroxy compound D or D* to create compound E or E*, wherein the E* has a second benzyl group at the nitrogen atom instead of the phenyl fluorenyl group in compound E, respectively:

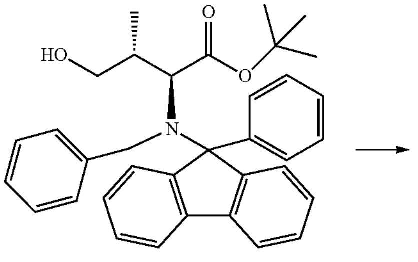

D

-continued

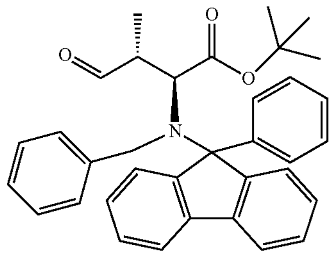

E;

(c) conversion of E or E* to create compound 4 or 4*, wherein the 4* has a second benzyl group at the nitrogen atom instead of the phenyl fluorenyl group in compound 4, respectively:

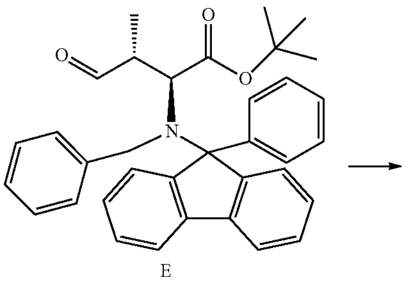

E

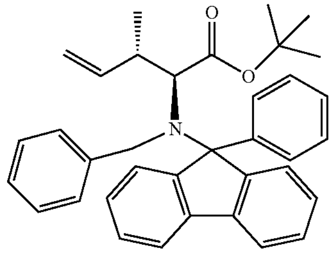

4;

(d) conversion of 4 or 4* to create compound F or F*, wherein the F* has a second benzyl group at the nitrogen atom instead of the phenyl fluorenyl group in compound F, respectively:

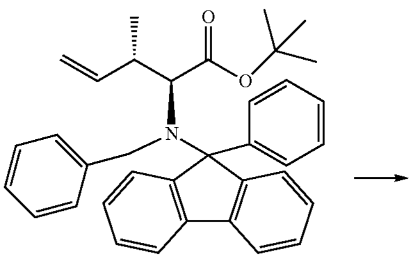

4

-continued

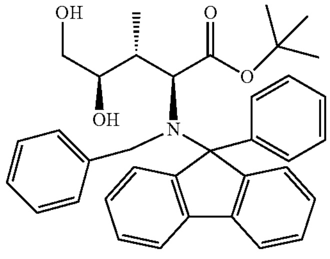

F;

(e) conversion of F or F* to create compound 5 or 5*, wherein the 5* has a second benzyl group at the nitrogen atom instead of the phenyl fluorenyl group in compound 5, respectively:

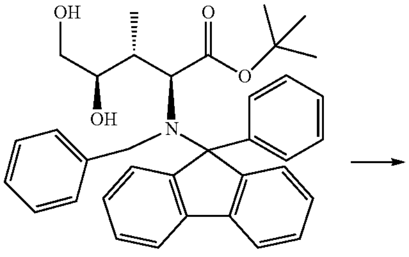

F

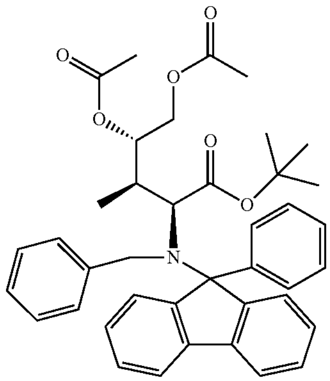

5;

(f) N-deprotection of 5 or 5* to create compound 6:

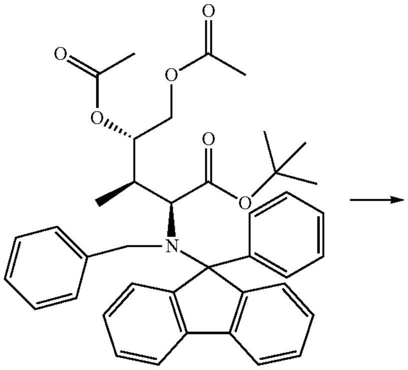

5

-continued

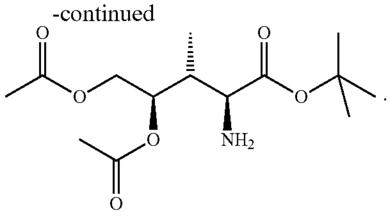

6

5. The method of claim 1, further comprising the step of isolating and purifying compound 6.

6. A compound of structure 6:

6

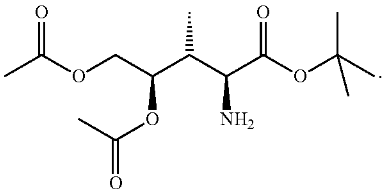

7. The compound of claim 6, wherein the compound has a purity greater than 90%.

8. The compound of claim 6, wherein the compound has a diastereomeric purity greater than 70:30.

9. A kit comprising the compound of claim 6, and one or more additional reagents for the synthesis of amatoxins or precursors thereof.

10. The kit of claim 9, wherein said one or more additional reagents are selected from the list of:

(i) a resin;

(ii) a protected hydroxyproline;

(iii) a protected asparagine;

(iv) a protected Cys-Trp dipeptide;

(v) a protected glycine;

(vi) a protected isoleucine;

(vii) a peptide coupling reagent;

(viii) a tertiary amine;

and combinations thereof.

11. A method for synthesizing an amatoxin, or precursor molecule therefore, comprising the step of (a) coupling compound 6 to hydroxyproline L to create compound G:

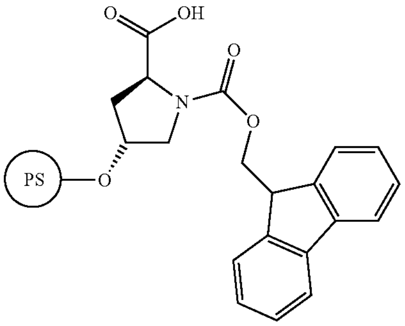

L

+

-continued

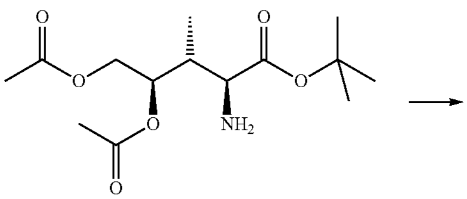

6

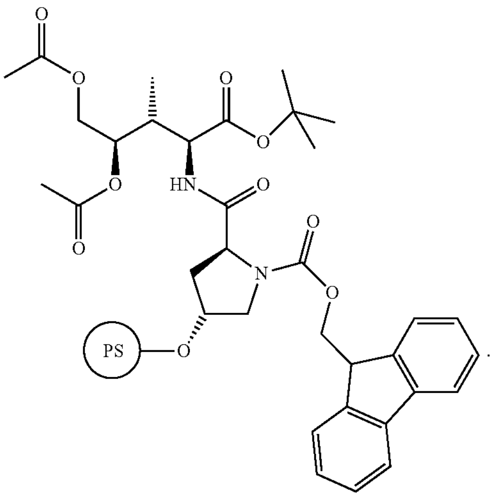

G

12. The method of claim 11, further comprising at least one of (b), (c), (d), and (e):

(b) iterative Fmoc-N-deprotection and coupling of G with Fmoc-(N-Tri)Asn OH; FmocCys(S-2-((o-$NO_2$Ph) $SO_2$Trp-O-Allyl))]OH, Fmoc-Gly OH, Fmoc-lle OH, and Fmoc-Gly OH to create compound H:

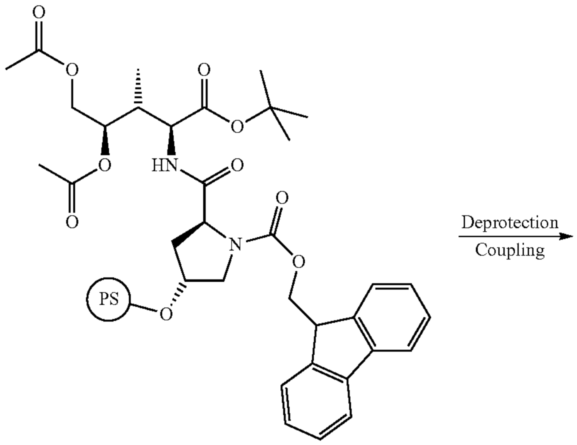

G

-continued
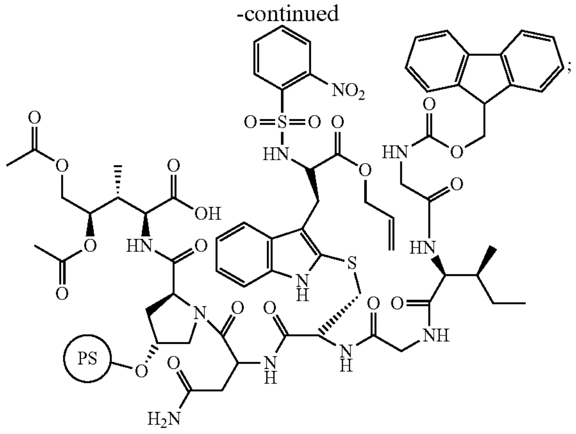
H
(c) O-allyl- and Fmoc-N-deprotection of H followed by cyclisation to create compound I:
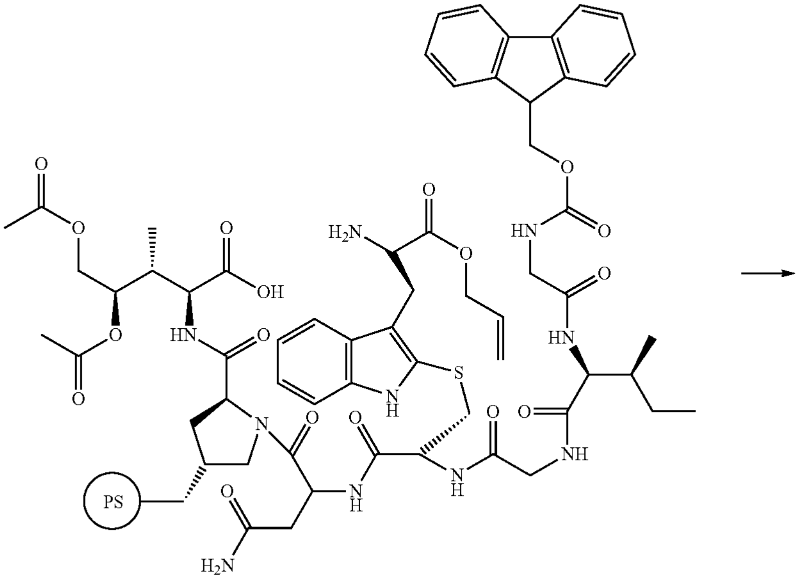
H
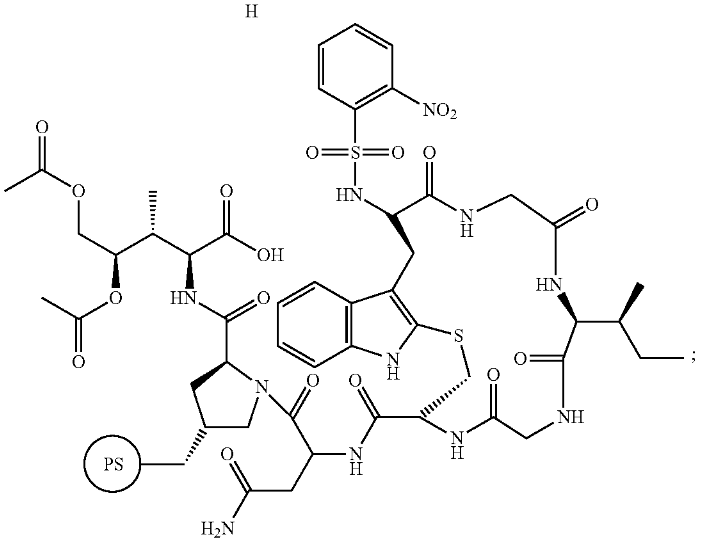
I (d) 2-nitro aryl sulfonamide-N-deprotection and secession of I from resin to create compound J:
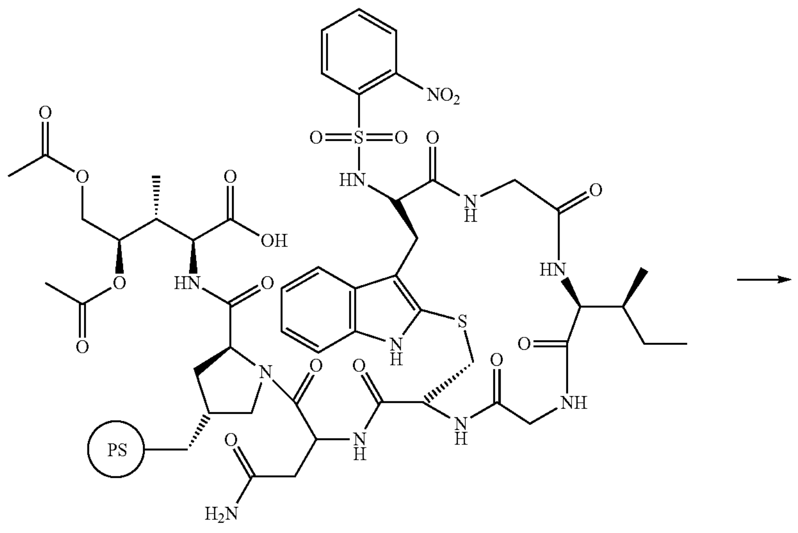
I
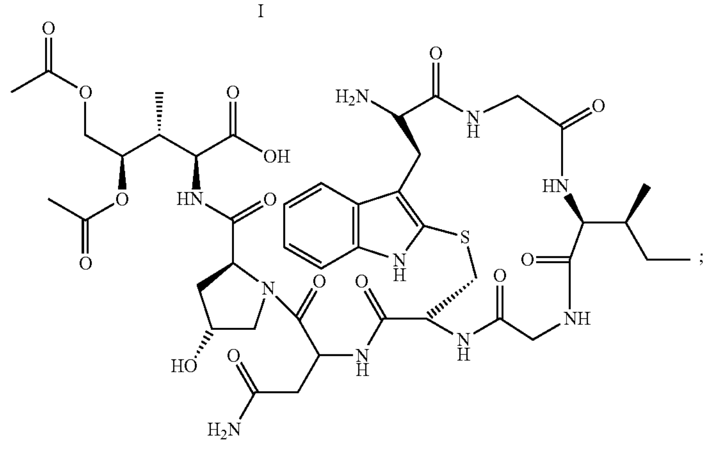
J
(e) solution phase cyclisation of J creating Amanitin derivative K:
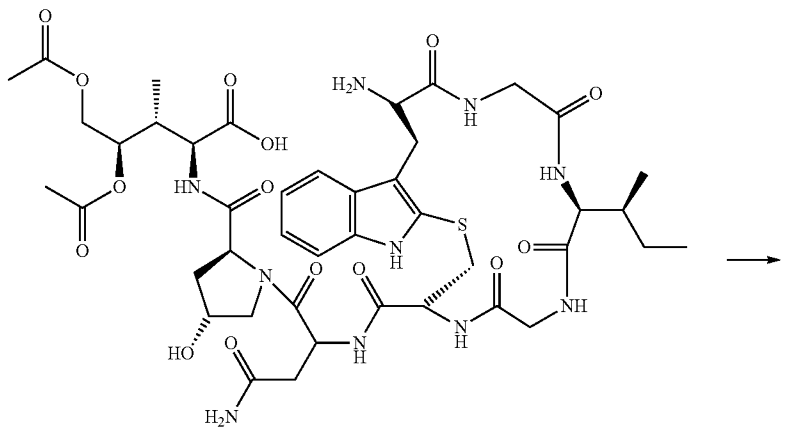
J -continued

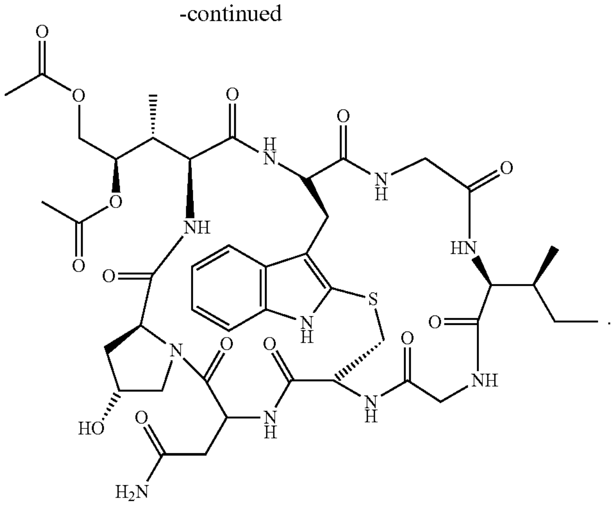

K

13. The method of claim 11, wherein the amatoxin comprises an amatoxin with a dihydroxyisoleucine moiety as its third amino acid.

14. The method of claim 4, comprising at least one of:

(i) the reduction of compound 2 or compound 2* in (a) with diisobutylaluminium hydride;

(ii) the oxidation of hydroxy compound D or D* in (b) using a Swern oxidation;

(iii) the conversion of E or E* in (c) under conditions of a Wittig reaction;

(iv) the conversion of 4 or 4* in (d) under conditions of a Sharpless oxidation;

(v) the conversion of F or F* in (e) under catalytic esterification conditions; and (vi) the N-deprotection of 5 or 5* in (f) using Palladium-catalyzed hydrogenation.

15. The kit of claim 10, wherein the resin is a Merrifield resin, a Rink-Amid resin, a THP-resin, or a combination thereof.

16. The kit of claim 10, comprising at least one of: a fluorenylmethyloxycarbonyl-(Fmoc-)-protected O-allyl hydroxyproline (FmocHypOAll); an Fmoc-protected N-trityl asparagine (Fmoc(N-Tri)AsnOH); an Fmoc-protected Cys-Trp dipeptide with -SH and -OH protection groups (FmocCys(S-2-((o-$NO_2$Ph)$SO_2$Trp-O-Allyl))]OH); an Fmoc-protected glycine (FmocGly); an Fmoc-protected isoleucine (FmocIle); a peptide coupling reagent selected from the group consisting of: O-(benzotriazol-1-yl)-N,N,N',N'-tetramethyluronium tetrafluoroborate (TBTU), benzotriazol-1-yl-oxytripyrrolidinophosphonium hexafluorophosphate (PyBOP), and o-(7-azabenzotriazol-1-yl)-N,N,N',N'-tetramethyluronium hexafluorophosphate (HATU); and N,N-diisopropylethylamine (DiPEA).

17. The method of claim 11, wherein compound 6 is coupled to hydroxyproline by reacting compound 6 with a hydroxyproline-preloaded resin.

18. The method of claim 17, wherein compound 6 is coupled to the free C-terminus of FmocHypOH immobilized on a resin L.

19. The method of claim 18, wherein the resin L is a tetrahydropyranyl (THP) resin.

* * * * *